US010537425B2

(12) United States Patent
Richter et al.

(10) Patent No.: US 10,537,425 B2
(45) Date of Patent: Jan. 21, 2020

(54) SYSTEM AND METHOD FOR ASSEMBLING A FOLDED PERCUTANEOUS VALVE

(71) Applicant: Valve Medical Ltd., Tel Aviv (IL)

(72) Inventors: Yoram Richter, Ramat Hasharon (IL); Ety Weisz, Tel Aviv (IL); Boaz Schwarz, Bat Yam (IL); Eran Reuven, Ramat Gan (IL); Eran Jassby, Tel Aviv (IL); Yaron David, Reut (IL); Amir Harel, Tel Aviv (IL)

(73) Assignee: Valve Medical Ltd., Tel Aviv (IL)

( * ) Notice: Subject to any disclaimer, the term of this patent is extended or adjusted under 35 U.S.C. 154(b) by 371 days.

(21) Appl. No.: 15/479,703

(22) Filed: Apr. 5, 2017

(65) Prior Publication Data
US 2017/0202665 A1 Jul. 20, 2017

Related U.S. Application Data

(63) Continuation of application No. 13/894,293, filed on May 14, 2013, now Pat. No. 9,642,702.
(Continued)

(51) Int. Cl.
*A61F 2/24* (2006.01)

(52) U.S. Cl.
CPC .......... *A61F 2/2418* (2013.01); *A61F 2/2409* (2013.01); *A61F 2/2412* (2013.01);
(Continued)

(58) Field of Classification Search
CPC .... A61F 2/2403; A61F 2/2409; A61F 2/2412; A61F 2/2418; A61F 2/2427;
(Continued)

(56) References Cited

U.S. PATENT DOCUMENTS 6,733,525 B2  5/2004  Yang et al.
7,331,991 B2  2/2008  Kheradvar et al.
(Continued)

FOREIGN PATENT DOCUMENTS

CN  101010047 A  8/2007
CN  101361683 A  2/2009
(Continued)

OTHER PUBLICATIONS

Extended European Search Report for related EP Application No. 16191500.4 dated Nov. 18, 2016, 8 pages.
(Continued)

*Primary Examiner* — Ashley L Fishback
(74) *Attorney, Agent, or Firm* — Cadwalader, Wickersham & Taft LLP

(57) ABSTRACT

The invention provides a multi-component (modular) percutaneous valve device that includes a valve module having valve leaflets and a valve frame. The valve frame includes one or more, for example two, ring members and a plurality of masts. Also provided is a valve frame having specially designed pivot points at the connection between masts and first and second ring members to assist folding the valve module and minimizing delivery diameter. The valve frame may also include wire guides to facilitate combining the valve module with a support module. The masts or a ring of the valve frame may also include locking members, such as shafts for closing the valve module and securing the valve module to the support module. The support module includes corresponding locking members, such as spears that align with the shafts on the valve module for assembly and locking the valve module to the support module.

33 Claims, 13 Drawing Sheets

Related U.S. Application Data

(60) Provisional application No. 61/688,470, filed on May 15, 2012.

(52) U.S. Cl.
CPC .......... *A61F 2/2427* (2013.01); *A61F 2/2433* (2013.01); *A61F 2/2436* (2013.01); *A61F 2/2439* (2013.01); *A61F 2220/005* (2013.01); *A61F 2220/0033* (2013.01); *A61F 2220/0041* (2013.01); *A61F 2220/0075* (2013.01); *A61F 2230/0013* (2013.01); *A61F 2250/006* (2013.01)

(58) Field of Classification Search
CPC .................. A61F 2/2436; A61F 2/2439; A61F 2220/0033; A61F 2220/0041; A61F 2250/006
See application file for complete search history.

(56) References Cited

U.S. PATENT DOCUMENTS

| | | |
|---|---|---|
| 8,840,663 B2 | 9/2014 | Salahieh et al. |
| 2002/0002400 A1 | 1/2002 | Drasler et al. |
| 2002/0138138 A1 | 9/2002 | Yang |
| 2004/0260389 A1 | 12/2004 | Case |
| 2005/0075728 A1 | 4/2005 | Nguyen et al. |
| 2005/0137686 A1 | 6/2005 | Salahieh et al. |
| 2005/0283231 A1 | 12/2005 | Haug et al. |
| 2006/0195180 A1 | 8/2006 | Kheradvar et al. |
| 2006/0287717 A1 | 12/2006 | Rowe et al. |
| 2007/0016288 A1 | 1/2007 | Gurskis et al. |
| 2007/0203503 A1 | 8/2007 | Salahieh et al. |
| 2007/0276467 A1 | 11/2007 | Kalmann |
| 2008/0097586 A1 | 4/2008 | Pavcnik et al. |
| 2008/0200980 A1 | 8/2008 | Robin et al. |
| 2008/0275550 A1 | 11/2008 | Kheradvar et al. |
| 2009/0062907 A1 | 3/2009 | Quijano et al. |
| 2010/0185275 A1 | 7/2010 | Richter et al. |
| 2011/0172784 A1 | 7/2011 | Richter et al. |
| 2012/0022629 A1 | 1/2012 | Perera et al. |

FOREIGN PATENT DOCUMENTS

| | | |
|---|---|---|
| CN | 102292053 A | 12/2011 |
| JP | 2008-541863 A | 11/2008 |
| JP | 2010-279730 | 12/2010 |
| JP | 4842144 | 12/2011 |
| JP | 2012-521854 | 9/2012 |
| JP | 2013-517011 | 5/2013 |
| SU | 1271508 | 11/1986 |
| WO | WO 98/43556 | 10/1998 |
| WO | WO 02/076348 | 10/2002 |
| WO | WO 2004/016200 | 2/2004 |
| WO | WO 2007/099448 | 9/2007 |
| WO | WO 2008/010817 | 1/2008 |
| WO | WO 2008/150529 | 12/2008 |
| WO | WO 2010/117680 | 10/2010 |

OTHER PUBLICATIONS

International Search Report and Written Opinion from related PCT Application No. PCT/IB2013/001819 dated Feb. 3, 2014, 13 pages.
Invitation and Partial International Search Annex from related PCT Application No. PCT/IB2013/001819 dated Nov. 19, 2013, 5 pages.
Office Actions and response of related U.S. Appl. No. 13/894,293, field May 14, 2013, now U.S. Pat. No. 9,642,702: • Response to Notice to File Corrected Application Papers dated Mar. 13, 2017; • Notice to File Corrected Application Papers dated Jan. 11, 2017; • Notice of Allowance and After Final Consideration Program Decision dated Dec. 29, 2016; • Response to Final Rejection with After Final Consideration Program Request dated Nov. 9, 2016; • Applicant Initiated Interview Summary dated Nov. 7, 2016; • Final Rejection dated Sep. 13, 2016; • Amendment and Response to Non-Final Rejection with Extension of Time dated May 25, 2016; and • Non-Final Rejection dated Feb. 2, 2016.

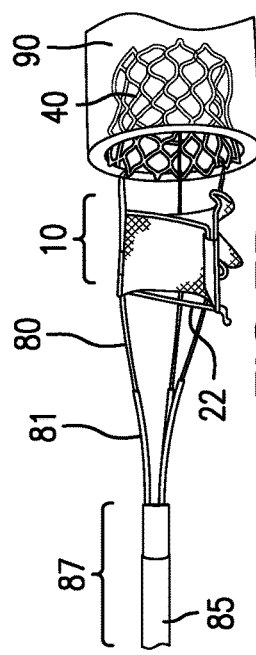
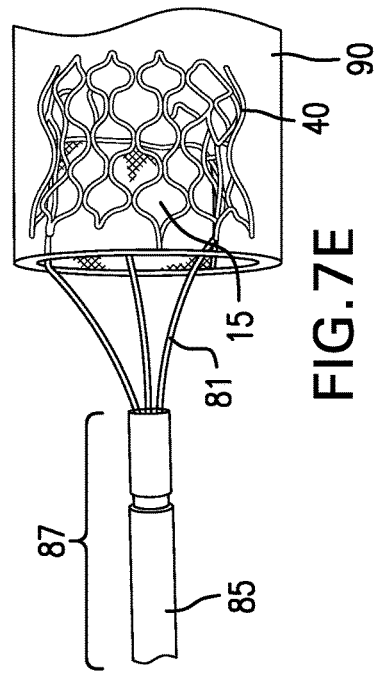
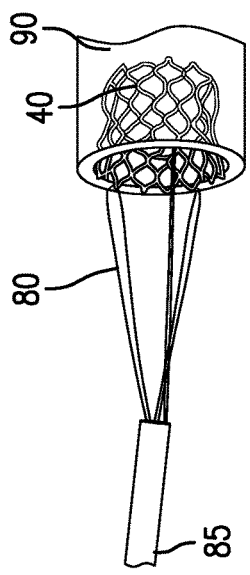
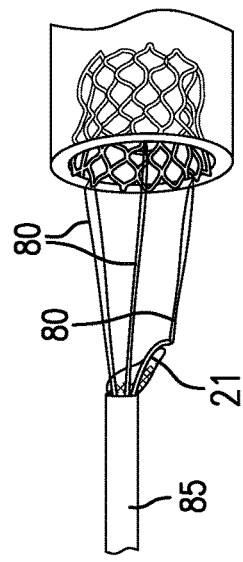
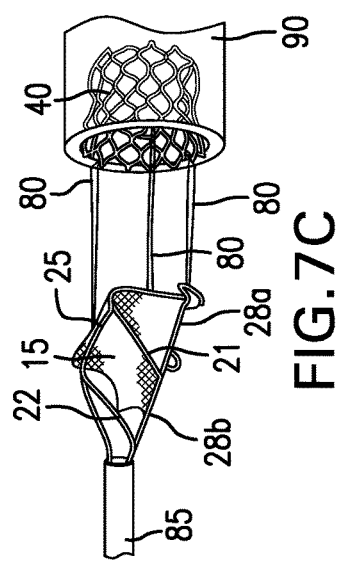

SYSTEM AND METHOD FOR ASSEMBLING A FOLDED PERCUTANEOUS VALVE

This application is a continuation of U.S. patent application Ser. No. 13/894,293 filed May 14, 2013 and claims benefit of priority to U.S. provisional application Ser. No. 61/688,470, filed May 15, 2012, which is incorporated herein by reference in its entirety.

FIELD OF INVENTION

The present invention relates to a system and method for deploying and assembling a modular percutaneous valve device. In particular, the modular valve device includes novel features to facilitate folding and assembly of the valve module, and the system includes novel features for deployment, combining and securing the device modules together.

BACKGROUND OF THE INVENTION

The human body contains a wide variety of natural valves, such as, for example, heart valves, esophageal and stomach valves, intestinal valves, and valves within the lymphatic system. Natural valves can degenerate for a variety of reasons, such as disease, age, and the like. A malfunctioning valve fails to maintain the bodily fluid flow in a single direction with minimal pressure loss. An example of a malfunctioning valve is a heart valve that may be either stenotic, i.e., the leaflets of the valve do not open fully, or regurgitant, i.e., the leaflets of the valve do not close properly. It is desirable to restore valve function to regain the proper functioning of the organ with which the valve is associated. For example, proper valve function in the heart ensures that blood flow is maintained in a single direction through a valve with minimal pressure loss, so that blood circulation and pressure can be maintained. Similarly, proper esophageal valve function ensures that acidic gastric secretions do not irritate or permanently damage the esophageal lining.

Several percutaneous prosthetic valve systems have been described. One example described in Andersen, et. al. (U.S. Pat. No. 5,411,552) comprises an expandable stent and a collapsible valve which is mounted onto the stent prior to deployment. The collapsible valve may be a biological valve or it may be made of synthetic material. The Anderson prosthetic valve is delivered and deployed using a balloon catheter which balloon is used to expand the valve-stent prosthesis to its final size. See also, U.S. Pat. No. 6,168,614 (Andersen, et al.) entitled "Valve Prosthesis for Implantation in the Body" and U.S. Pat. No. 5,840,081 (Andersen, et al.) entitled "System and Method for Implanting Cardiac Valves."

Spenser, et. al. (U.S. Pat. No. 6,893,460) describe another prosthetic valve device comprising a valve structure made of biological or synthetic material and a support stent. The Spenser prosthetic valve is a crimpable leafed-valve assembly consisting of a conduit having an inlet and an outlet, made of pliant material arranged to present collapsible walls at the outlet. The valve assembly is affixed to the support stent prior to deployment. The complete valve device is deployed at a target location within the body duct using a deploying means, such as a balloon catheter or a similar device.

Percutaneous implantation of prosthetic valves is safer, cheaper, and provides shorter patient recovery time than standard surgical procedures. However, current artificial percutaneous prosthetic valves have the disadvantage of being extremely bulky, even when compressed for delivery. The problem with this bulkiness is that it requires the delivery catheter to have a rather large diameter. Large catheters generally are not suitable for percutaneous procedures and require cut-down surgical procedures and/or sophisticated and difficult puncture-closure techniques. The bulkiness and large diameter of current valve devices and delivery systems combined with the anatomy through which the devices must be delivered also can make delivery into the lumen problematic from the point of view of success rate, accuracy of deployment, and risk of complications. Specifically, delivery complications may arise due to the shape of the lumen, for example, the significant natural curve of the aortic arch and/or a tortuous iliac/femoral artery through which the catheter is introduced. Further, a catheter of such diameter tends to be less flexible than a smaller diameter catheter, especially when loaded with a bulky, inflexible device. Additionally, manipulating such a loaded catheter through a narrow vessel, and in particular a curved vessel, substantially raises the potential for damage to that vessel wall, bleeding, and other vascular complications, which are in turn related to higher rates of morbidity and mortality.

Still further, the valve leaflet material makes up 80% of the percutaneous prosthetic valve delivery diameter. Current efforts to minimize the bulk of the valve leaflet material include using thinner valve material or tightly crimping the valve leaflets. Both of these procedures adversely impact the durability of the valve leaflets, the latter does so by damaging the valve material.

Therefore, a need exists to facilitate the delivery of artificial valves and also to increase the safety of the procedure. A valve device having a smaller delivery diameter than pre-assembled percutaneous valve devices and that can be delivered through a vessel without incurring further damage to the wall of the body lumen is highly desirable. It is also desirable to have a low profile (small delivery diameter) percutaneous prosthetic valve device that provides the type of leaflet durability available in surgical prosthetic valve devices.

US Published Patent Application No. 2010/0185275A1, incorporated herein by reference in its entirety, describes a modular (multi-component) percutaneous valve device that facilitates delivery of the prosthetic valve by providing the valve device as deliverable modules that may be assembled into a working configuration at or near the site of implantation in the blood vessel. US Published Patent Application No. 2010/0185275A1 also describes various means for locking together the assembled device modules.

US Published Patent Application No. 2011/0172784A1, incorporated herein by reference in its entirety, describes a modular (multi-component) percutaneous valve device having a self-assembly member that facilitates assembly of the modular prosthetic valve in the blood vessel. US Published Patent Application No. 2011/0172784A1 also describes valve modules that may assume a shape (unassembled shape) different from their functional valve shape that are particularly advantageous for delivery in that the unassembled shape permits the valve module to be folded in a manner that minimizes the delivery diameter of the device, thereby minimizing complications and increasing the safety of the valve replacement procedure.

SUMMARY OF THE INVENTION

The present invention provides an improved modular percutaneous valve device and system, having components that simplify the assembly of the device modules. In particular, a system and method for deploying and assembling a percutaneous modular valve device is provided. The multi-component, or modular, percutaneous valve device and system comprises a plurality of device modules for delivery. In one embodiment, the plurality of device modules includes a valve module and a support module, which are designed to be combined into the assembled valve device in the body. From a functional perspective, the valve module is the portion of the valve device having the leaflets and once assembled it provides a conduit having an inlet end and an outlet end. The support module provides the anchor, or backbone, of the device, housing the valve module and holding the valve module in place within the body lumen. In percutaneous valve replacement procedures the native valve leaflets often are not removed prior to implantation of the prosthetic valve; thus the support module also serves to outwardly displace the native valve leaflets to create a larger valve orifice, in particular when the prosthetic valve is used to treat aortic stenosis.

The valve module of the invention is provided with a valve frame having one or more ring members, and a plurality of masts connected thereto. The one or more ring members are discontinuous, each having a first end and a second end, thereby permitting the ring members to be opened for folding. This provides a valve module having an unassembled, folded delivery configuration, in which the one or more open ring members and the masts are substantially collinear, and the valve leaflets folded therewith. The terms collinear and substantially collinear are used interchangeably herein, and are meant to convey extending in the same general direction and/or linearly adjacent. Thus, for example, in the delivery configuration, the "folded" masts lie approximately parallel to the one or more ring members. In one embodiment, one of the masts may be a split mast, the first half of which is located at the first end of the ring member(s) and the second half is located at the second end of the ring member(s).

The valve module also has a working configuration in which the ends of the ring member(s) are approximate (i.e., close together, next to each other) so as to form a ring, and the masts are oriented along the longitudinal axis of the valve, generally upright relative to the ring member(s). The valve leaflets are attached to a ring member, for example a ring member at the base of the valve module, and in the embodiment having a first and second ring member the valve leaflets may be supported by the second ring member. Alternatively, or in addition, the valve leaflets may be supported by one or more of the plurality of masts.

The support module has a compressed delivery configuration and an expanded working configuration, into which the valve module may be inserted and attached. In one embodiment, the support module has a radially compressed delivery configuration and is radially expandable to the working configuration.

The valve module and support module may further include novel structures that collectively facilitate guiding the valve module to the support module for combination therewith, closing the valve module to form a conduit, and locking the valve module to the support module. These novel features may include shafts and spears, wire guides, and assembly wires. The spears may include eyelets for cooperative use with the wire guides to guide the valve along assembly wires into the support module. Elements such as wire guides, eyelets and assembly wires are also referred to herein as "guiding members." The shafts and spears function as locking members to lock the valve module to the support module. Other types of locking members also may be used, for example, snaps or other geometric locking mechanisms. The relative position of the locking members may differ depending on the embodiment. For example, the shafts may be located on a component of the valve frame and the spears may be located on the support module. Alternatively, the spears may be located on the valve frame and the shafts may be located on the support module.

In one embodiment in which the valve frame includes a first and second ring member with the plurality of masts disposed therebetween, the connections between the masts and ring members may be novel pivot point connections. The pivot point connections facilitate folding of the valve frame while minimizing physical strain on the connections. In another embodiment the valve frame comprises a first ring member at the base with the plurality of masts connected thereto via novel pivot point connections.

The system of the invention includes the above-described modular valve device, and a delivery system that includes a catheter and assembly wires. In certain embodiments, the delivery system further comprises pushers that may be advanced over the assembly wires to slide the valve module over the assembly wires into the support module, and may further be used to lock the locking members. In embodiments that include wire guides, each assembly wire may be threaded through wire guides to minimize tangling of the assembly wires. In embodiments in which the support module includes spears having eyelets, the assembly wires may additionally be threaded through the eyelets, to facilitate disengagement of the wire from the valve device once implanted by pulling on one end of the wire. Alternatively, the assembly wire may be threaded through a portion of the valve frame and/or the support module.

Also provided is a method of assembling the modular percutaneous valve device using the novel components of the system. The valve module is advanced over assembly wires and the wire guides are useful for orienting and assembling the valve module, and combining the valve module with the expanded support module. In one embodiment, the valve module may include shafts (tubular or ring structures) and the support module may include spears, specialized structures for connecting with the shafts, attached at positions around the circumference of the support module that correspond to the positions of the shafts. The shafts may be located, for example, on the masts and/or on a ring member. When located on masts of the valve frame, the shafts may be located on the outer surface or the inner surface of the masts, or some combination thereof. In another embodiment, the shafts may be located on the support module and the spears may be located on the valve module. In either embodiment, the shafts may be eased over the spears and may lock in place. Where a split mast is used, the split mast may include a pair of shafts—one on each half of the split mast—which, in combination with a spear on the support module, simultaneously close the ring members to effect a working configuration valve module and effect locking the valve module to the support module.

Among the advantages of the modular percutaneous valve of the present invention are a valve module that easily folds for delivery, readily transforms to a near assembled configuration upon deployment from a delivery device, and provides support for the valve leaflets. Advantages of the system of the invention include a design that facilitates unfolding and assembly of the valve module into the working configuration, aligning the valve module with the support module for combining the device modules, and securing the device modules to each other. Another advantage of the present invention is that because the valve device is modular, the properties of the modules may be optimized independently, because the valve module and support module serve different functions—the valve module modulating blood flow and the support module anchoring the valve in the valve annulus and pinning back the native valve leaflets; separately deploying the modules and combining them in situ lessens the design trade-offs that are necessary when the valve device is a single unit.

Other advantages that may be achieved by the present invention include reducing the bulkiness of the valve for delivery while maintaining durability of the valve leaflets, and increasing the flexibility of the delivery device. Also, the prosthetic valve device is minimally invasive and the method of percutaneous delivery reduces traumatic damage and minimizes procedure complications, and allows delivery to patients with smaller vessels, with highly diseased, tortuous or occluded vessels, and reduces the risk of vascular complications. Use of the apparatus, system and methods of the invention thereby may increase the safety of the procedure and expand both the number of medical facilities capable of performing percutaneous valve replacement procedures and the number of patients who can receive the treatment.

BRIEF DESCRIPTION OF THE DRAWINGS

FIG. 3A schematically illustrates the valve frame in its unassembled substantially flat configuration; FIG. 3B schematically depicts how a ring member and mast are connected at the horseshoe pivot point of the valve frame embodiment of FIG. 3A.

FIG. 4A illustrates a top view of the valve frame embodiment of FIG. 3A; FIG. 4B illustrates a side view of the valve frame embodiment of FIG. 3A.

FIGS. 7A-E are photographs illustrating a method of deploying and assembling an embodiment of the modular valve device according to the invention.

FIG. 8A is a schematic drawing of a photograph depicting how a shaft on a valve module may connect to a spear having a deltoid or "kite" spearhead on a support module; FIG. 8B illustrates the same schematically.

FIG. 9A is a schematic drawing of a photograph illustrating a wire guide and first and second shafts on a valve module, and an assembly wire threaded through these structures. FIG. 9B schematically illustrates how the first and second shafts of FIG. 9A may connect to a spear of a support module.

FIG. 10A is a schematic drawing of a photograph illustrating how a ring shaft on a valve module may connect to a hybrid spear on a support module; FIG. 10B is an inset depicting the ring shaft locked on the hybrid spear.

FIG. 11A schematically illustrates the hybrid spear; FIG. 11B schematically illustrates a ring shaft being introduced onto the hybrid spear; FIG. 11C schematically illustrates the ring shaft locked on the hybrid spear.

FIG. 12A shows the embodiment from front view coupled with a mast via ring shafts; FIG. 12B is a cut-away of the same view to reveal the spear and ring structures.

FIG. 13A shows the embodiment from front view coupled with a split mast via shaft and ring shaft; FIG. 13B is a cut-away of the same view to reveal the spear, shaft and ring shaft structures.

DETAILED DESCRIPTION OF THE INVENTION

Figure 1:
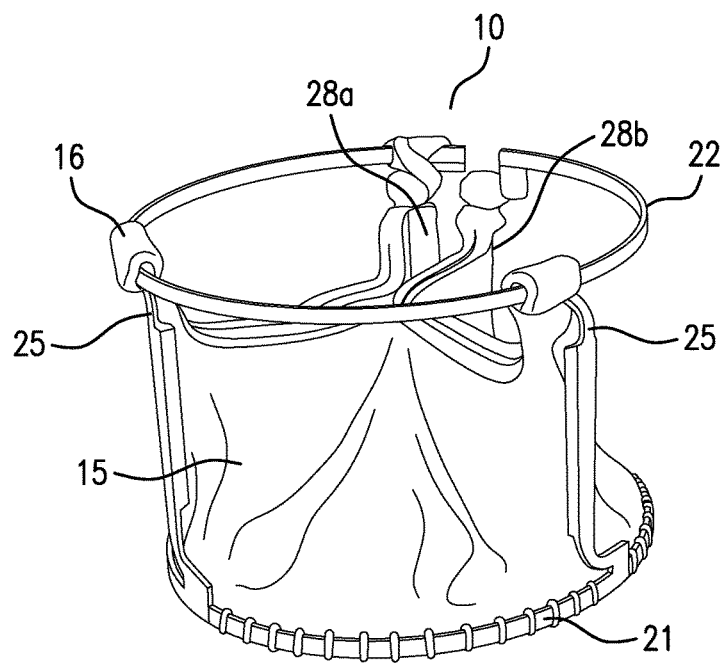
FIG. 1 is a schematic drawing of a photograph illustrating a double ring embodiment of the valve module of the invention.

The present invention provides an implantable modular percutaneous prosthetic valve device, system and method for deploying and assembling implantable percutaneous modular valve devices, for example percutaneous modular heart valve devices.

The percutaneous valve device of the invention comprises a plurality of device modules for delivery and assembly in a body lumen, for example a blood vessel. The device modules may be delivered percutaneously to a desired location in the body, for example near the site of valve implantation or at the site of valve implantation, where they may be deployed from the delivery device and assembled to form a working valve device. The plurality of device modules may include a support module and a valve module. The support module has a compressed delivery configuration and an expanded working configuration. The valve module comprises the valve leaflets of the valve device and a valve frame; the valve leaflets may be attached to components of the valve frame, which include one or more ring members and a plurality of masts connected thereto.

The valve module has an unassembled open configuration, in which the one or more ring members have a substantially linear, i.e., generally straight, configuration and the valve leaflets lie substantially flat. One skilled in the art understands that valve leaflets have a shape, e.g., including commissures, and therefore the term "substantially flat" may include some undulations. This unassembled open configuration permits folding, e.g., rolling, of the valve module predominantly "lengthwise" into a folded delivery configuration, and from which the valve module may be assembled into a working configuration. In the unassembled open configuration, the valve module has a width along its longitudinal axis, i.e., apex to base, and a length along the linear circumferential axis, i.e., along an axis defined between the first end of the one or more ring members and the second end of the one or more ring members (or in embodiments having a split mast, between the first mast half and the second mast half). Therefore, "lengthwise" is understood by one having ordinary skill in the art to mean along the length, e.g., from one split mast half to the second split mast. In its folded configuration, the plurality of masts may be folded toward the one or more ring members so as to be substantially collinear with the substantially linear ring members.

The "lengthwise" folding of the valve module facilitates a delivery configuration having a minimal diameter and minimizes crimping damage to the leaflets, thereby improving durability. In particular, folding the valve module predominantly lengthwise distributes the bulk of the leaflet material over a greater axial distance than folding or compressing radially, so that there is less valve material at any one point in the delivery catheter. As a result, less crimping force is required on the leaflets, compared to radial crimping of currently marketed devices, to achieve a small delivery diameter. The resultant advantage is less crimping damage to the leaflet material, and thus improved durability. Additionally, it isn't necessary to use a thinner valve material to achieve the small delivery profile. One example of such advantageous predominantly lengthwise folding comprises rolling the open unassembled valve module spirally, for example around a guide wire. Another example is scrunching the valve material as the plurality of masts are folded toward the one or more ring members.

In some embodiments, specialized connections between the masts and ring members—pivot points—may facilitate the folding. When assembled into a working configuration, the valve module provides a conduit having an inlet end and an outlet end. The valve frame may include, in its working configuration, one or more ring members with ends approximated and a plurality of masts oriented along the longitudinal axis of the valve, thereby—with the valve leaflets—forming a conduit. The valve leaflets may be supported by one or more of the ring member(s) and masts.

The valve frame may be manufactured from any of a variety of materials, such as, for example, a shape-memory alloy, cobalt chromium, a material having superelastic properties, or a polymeric deformable plastic. In one embodiment, the valve frame comprises a shape-memory metal or alloy, pre-conditioned to revert to a preset configuration. In one aspect of this embodiment, the valve frame is made from a shape-memory alloy. The preset configuration may be referred to as a first configuration (e.g., a relaxed state) and the delivery configuration may be referred to as a second configuration (e.g., an unrelaxed, or restrained state). The valve frame may be triggered to revert to the preset configuration by, for example, a change in temperature (heating or cooling), an electrical current, or if it has superelastic properties it may be released from a geometric restriction, or it may be mechanically deformed or "triggered" by balloon expansion, which, for example, may trigger conversion of, for example, NiTi to a different phase. The shape memory alloy allows the valve frame to be thermo-mechanically preconditioned into a preselected shape (pre-set configuration), so that in one embodiment it may be delivered in, for example, a relatively straight, but axially flexible second configuration and then be triggered to revert to the thermo-mechanically preset first configuration. In another embodiment, the delivery device, or a lumen within the delivery device, may restrain the valve frame in a delivery configuration, and the trigger may be a release from the restraint.

As used herein, "preset configuration" or "first configuration" with respect to valve frame is not limited to shape-memory structures. By "preset configuration" and "first configuration" is meant the pre-selected shape that the valve frame assumes or reverts to after deployment from the delivery device. Where the valve frame is reverted to its first configuration, for example by a temperature step, the temperature step may be effected by changing the temperature in the environment around the valve frame, for example by hot fluid, cool fluid, body heat, or passing electrical current through a wire to generate resistive heat. Any shape memory alloy may be used to make the shape memory valve frame. In specific embodiments, the shape memory alloy used is NiTi (i.e., NiTinol), CuZnAl, CuAlNi, or a mixture thereof (see, e.g., SHAPE MEMORY MATERIALS, edited by Otsuka and Wayman, Cambridge University Press; October 1999 and SHAPE MEMORY ALLOYS, edited by Youyi and Otsuka, International Academic Publishers, June 1998).

The valve leaflet material may be manufactured from suitable materials, such as polymers, metals or biological material, such as mammalian pericardium derived from, for example, bovine, porcine or equine tissue. The selection of material, structure and method of manufacturing preferably is made to optimize the function, the durability and the biocompatibility of the valve. The valve leaflets may be attached to the valve frame by means known in the art, for example by sewing, gluing, bonding, or by the method described hereinbelow.

The support module preferably is expandable, so that it may be delivered compressed (unexpanded), and then expanded for implantation and assembly of the valve device. The support module may be manufactured from a biocompatible material that is sufficiently durable that the structure can support the valve component while maintaining the device's position in the lumen. The support module material also is compatible with delivery of the support module in a compressed state and expansion of the compressed support module upon deployment in the lumen. For example, the support module may be manufactured from a variety of materials including a shape-memory alloy, cobalt chromium, a material having superelastic properties, or a polymeric deformable plastic. In one embodiment of the present invention, the support module is manufactured from stainless steel or a shape memory alloy, such as, for example, Nitinol. In another embodiment, it may be made of an amorphous metal alloy of suitable atomic composition, as are known in the art. Other further embodiments of the support module may be manufactured from similar biocompatible materials known in the art. One non-limiting example of an appropriate support module is a mesh tube. In this example, the support module comprises a hollow, generally cylindrical (annular) member having a side surface comprising a mesh having a plurality of apertures or cells. The support module possesses sufficient radial strength to maintain its position at the implantation site once the support module is deployed, to outwardly displace native valve leaflets, and to create a larger valve orifice than that of a diseased valve to be replaced. The support module, may be self-expanding or balloon-expandable. Examples of support modules for use in the invention are known in the art.

The support module may include locking members, such as those described herein, to secure the valve module within the support module. The support module may further include hooks, ribs, or other anchoring devices to facilitate the anchoring of the assembled valve device to the native anatomy, e.g., the valve annulus. The connection of the support module to the valve annulus and/or of the valve module to the support module may be designed to provide adjustment to the relative positions of the structures.

The devices and methods of the invention are particularly adapted for use in percutaneous aortic valve replacement, but may also find use as replacements for other cardiac valves, such as, e.g., pulmonic, mitral, and tricuspid valves, as well as valves in the peripheral vasculature or in other bodily lumens, such as the alimentary canal, lymph ducts, the biliary duct, and any other lumens having valves requiring replacement or needing valve implantation. Where the modular valve device is designed to replace an aortic valve, it may be assembled in the ascending aorta, the descending aorta, the left ventricle, at the implantation site, or part at the implantation site and part in the aorta. Although particularly adapted for use in lumens of the human body, the devices, systems, and methods may also find application in animals.

The aforementioned embodiments as well as other embodiments are discussed and explained below with reference to the accompanying drawings. The drawings are provided as an exemplary understanding of the present invention and to schematically illustrate particular embodiments of the present invention. The skilled artisan will readily recognize other similar examples equally within the scope of the invention. The drawings are not intended to limit the scope of the present invention as defined in the appended claims.

As noted above, the modular valve device of the invention comprises a valve module and support module, which may be delivered in unassembled delivery configurations and assembled and combined after deployment from a delivery device. The valve module comprises valve leaflets attached to a valve frame. Exemplary depictions of a partially assembled valve frame and an expanded support module are illustrated in FIGS. 14A and 14B, respectively. Details of the valve module and its connection to the support module are set forth in FIGS. 1-13.

FIG. 1 illustrates a non-limiting embodiment of the valve module invention, in which the valve frame includes a first and second ring member. As illustrated in FIG. 1, the valve module 10, in its assembled working configuration, includes valve leaflets 15 and a valve frame. The valve frame includes a first ring member 21 at the base of the valve module (proximal end of the valve) and a second ring member 22 at the distal end of the valve module (distal end of the valve) and a plurality of masts 25, 28a, 28b, for example three masts, extending generally perpendicularly therebetween connecting the first and second ring members 21, 22. In one embodiment, the first ring member 21 is wider along the longitudinal axis than the second ring member 22 (see FIG. 14A), making the first ring member more resistant to warping, thereby maintaining the shape of the assembled valve module.

The valve leaflets 15 may be attached to one or both ring members 21, 22 and/or masts 25, 28a, 28b. In the embodiment depicted in FIG. 1, the valve leaflets 15 are attached to the first ring member 21 and suspended from the second ring member 22, for example at points adjacent the connection points between the masts 25, 28a, 28b and the second ring member 22. FIG. 1 also illustrates an embodiment in which the valve leaflets 15 are attached to the split mast 28a, 28b but not the other masts 25. The valve leaflets 15 may be attached to the valve frame, for example, by sewing as illustrated in FIG. 1, or by any other appropriate method known in the art. For example, the valve leaflets 15 may be suspended via leaflet loops 16, as illustrated in FIGS. 1, 5, 6A and 6B. Alternatively, the valve leaflets 15 may be suspended or attached, e.g., by sewing, to a second ring member 22 or a mast 25, 28a, 28b, or by other means within the skill in the art. The leaflet loops 16 may be made from the same material as the valve leaflets 15 and fastened by, for example, sewing the loop closed, sewing the loop to the second ring member 22, or some combination thereof. Alternatively, the valve leaflets 15 may be suspended from the second ring member 22 by a loop formed of sewing thread or a second material.

In one embodiment, rather than being attached directly to the valve frame, the valve leaflet material (first material) is attached to a second, flexible, more durable material, which in turn is affixed to the valve frame by means known in the art, e.g., looping, sewing, gluing, bonding. One embodiment for attaching the valve leaflets to the valve frame is a sandwich attachment. Specifically, in this aspect, the second material is wrapped around a portion of the valve frame, for example a ring member or a mast, with sufficient segments of second material beyond the wrapping to allow a segment of the first material to be inserted between the two segments of the second material to form a first material-second material-first material (three-layer) sandwich. The second material may then be attached to the first material, for example by sewing with, e.g., sutures. The first material may be, for example, pericardium and the second material may be, for example, Dacron, although other combinations of suitably materials known in the art also may be used.

The sandwich attachment embodiment may alternatively comprise an open sandwich (two layer). In this embodiment, the second material is wrapped around the valve frame and attached to itself leaving a tail, which may be separately attached to a segment of valve leaflet by means described above. Similar sandwich attachment designs may be used for attaching the valve leaflets to a mast, including use of tabs or loops to accommodate attachment points of locking members on the mast. An advantage of the sandwich attachment is improved longevity of valve integrity, as abrasion of the valve leaflet material (first material) by the surfaces of the valve frame is avoided.

Figure 2:
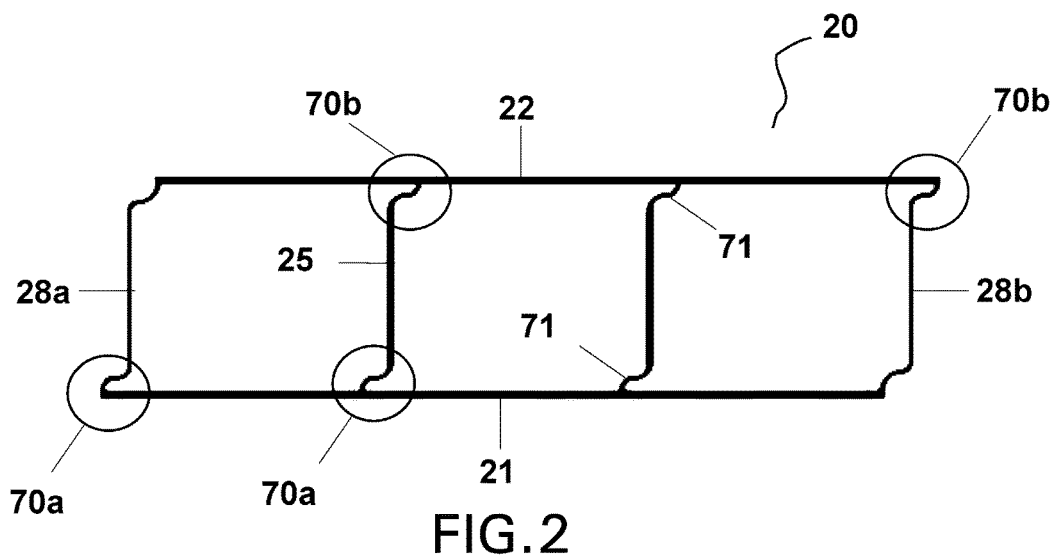
FIG. 2 schematically illustrates a valve frame in its unassembled substantially flat configuration, showing one embodiment of pivot points.
Figure 3A:
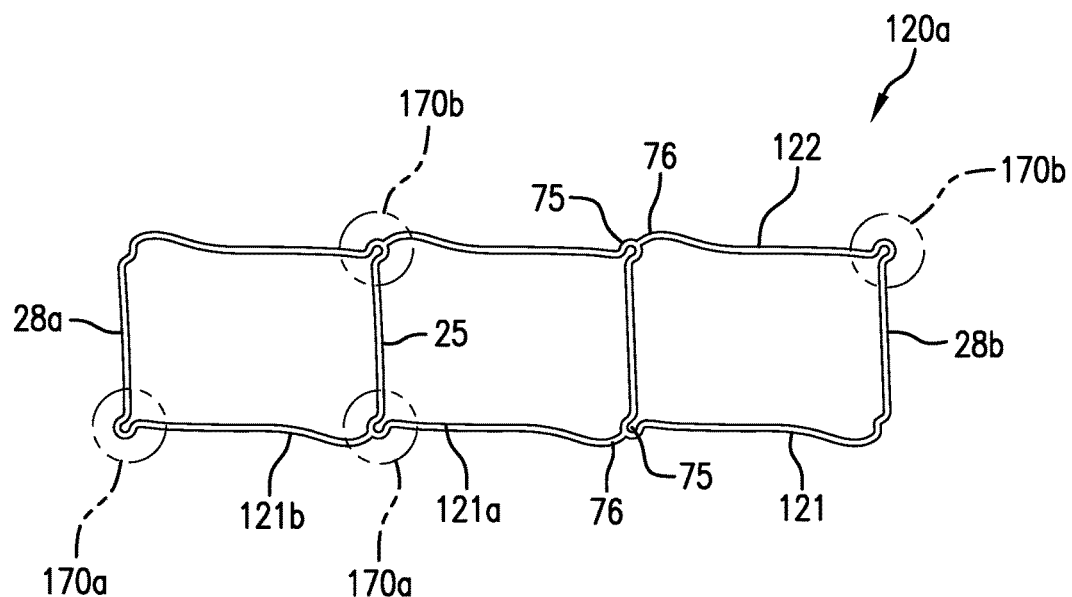
FIGS. 3A-B illustrate another embodiment of a valve frame having horseshoe pivot points.

In its unassembled folded configuration, the first and second ring members 22, 22 of FIG. 1 are not closed or substantially closed structures, but open: each is arranged in a substantially linear configuration, having a first end and a second end, as shown for example, in FIGS. 2 and 3A. In one embodiment, as illustrated in FIGS. 1, 2 and 3A (see also FIG. 9A), one of the masts is a split mast 28a, 28b, such that a first half of the split mast 28a is located at a first end of the unassembled valve module, connected to the first end of the ring member(s), and a second half of the split mast 28b is located at a second end of the unassembled valve module, connected to the second end of the ring member(s). The valve leaflets 15 may be secured to each half of the split mast 28a, 28b, for example by sewing, by the methods described above, or by any other appropriate method known in the art.

Figure 9A:
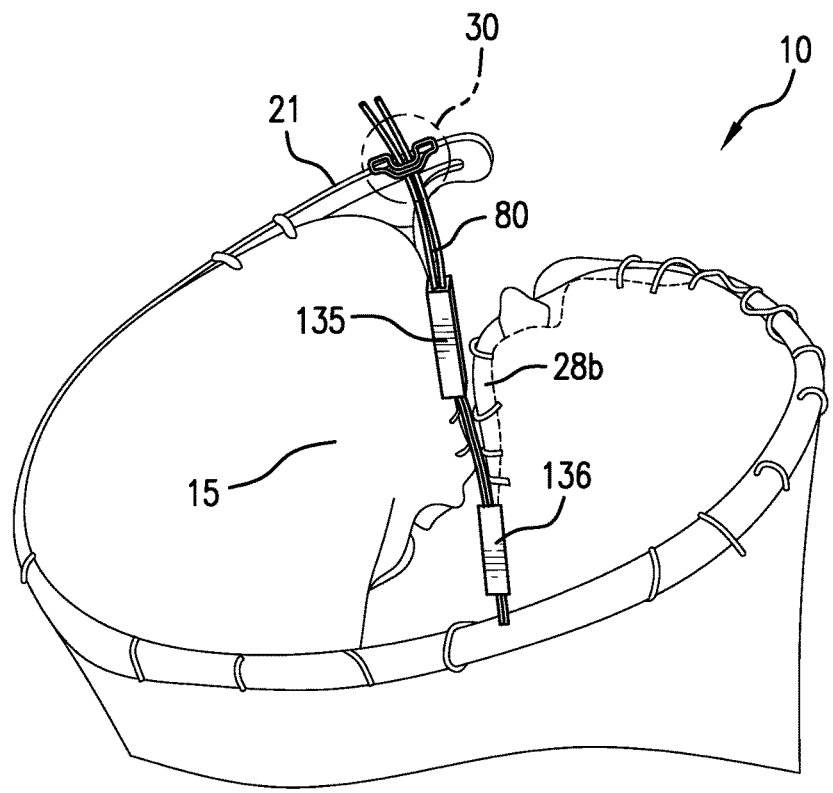
FIGS. 9A-B illustrate an embodiment of novel locking members.
Figure 9B:
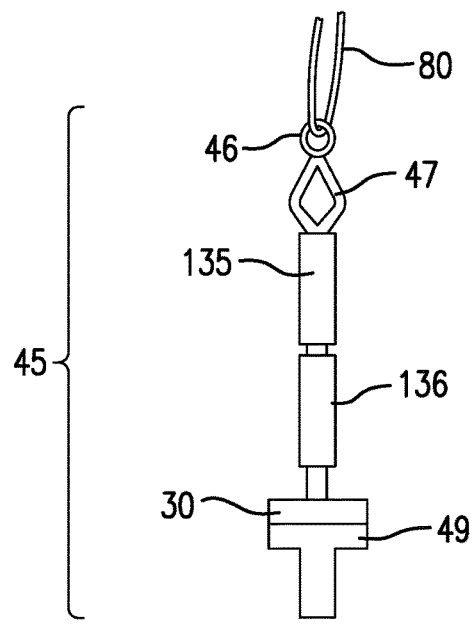

A ring member, as illustrated in FIG. 9A for a valve frame having a split mast, may be fitted with a wire guide 30, for example, adjacent the proximal end of a mast, through which an assembly wire 80 may be threaded. The proximal end is the end nearest the heart when the valve is implanted to replace an aortic valve. For example, as shown in FIG. 14A, a first wire guide 30 may be located on the first ring member 21 (see also FIG. 9A) near the first half of a split mast 28a, and second wire guide 31 may be located on the second ring member 22 near the second half of a split mast 28b. Similarly, a first wire guide 30 also may be located on the first ring member 21 near the proximal end of a mast 25 and a second wire guide 31 may be located on the second ring member 22 near the proximal end of the mast 25. While not a required feature of the valve frame, the wire guides 30, 31 are useful for maintaining proper alignment of the assembly wires 80 relative to the valve frame when deploying the valve module from the catheter.

When delivering the valve module, it must be folded to a delivery configuration having a small diameter, yet be able to readily transform to a near tubular configuration after deployment for assembly and combination with the support module. The present invention provides an improved valve frame structure for folding the valve module.

Folding the masts towards the ring members to form a substantially collinear folded valve frame, may cause significant stress or strain on valve frame material at the connection points between the masts and the first and second ring members. Thus in one aspect of the invention, the connection points may be designed as pivot points 70, shown, for example, in FIG. 2. Use of pivot points, as opposed to standard unelaborated connections, facilitates folding of the valve frame to permit the first and second rings and masts to be substantially collinear without causing significant material strain or stress at the connection points. Reduction in strains on the valve frame via the novel pivot points of the invention provides a further advantage of allowing a minimum cross section when the first and second rings and masts of the valve frame are folded so as to be substantially collinear. In one embodiment, the masts and first and second ring members are considerably stiffer than the pivot points. There are any number of ways to optimize pivot points to reduce the material strain or stress at the connection points, for example adjusting the plane, thickness, width or shape of the connection. Two non-limiting examples of pivot points that may be used, which employ shape, are described below, but based on this description one skilled in the art would understand other shapes that may be used for the inventive pivot points.

In one embodiment of a valve frame 20, depicted in FIG. 2, the novel pivot points 70a, 70b may be contained in the masts 25, 28a, 28b, substantially s-shaped 71, and connect to the first and second ring members 21, 22 at right angles. The orientation of the s-shape of the pivot point 70a connecting the first ring member 21 to a mast 25, 28a, 28b may be opposite (or the inverse) of the s-shape of the pivot point 70b connecting the second ring member 22 to a mast 25, 28a, 28b, as shown in FIG. 2. Compare 70a and 70b in FIG. 2. Preferably, the s-shaped pivot points 71 connecting masts to the first ring member 21 have the same orientation, and s-shaped pivot points 71 connecting masts to the second ring member 22 have the same orientation. The s-shaped pivot point illustrated in FIG. 2 may also have a narrower width than the masts.

Figure 3B:
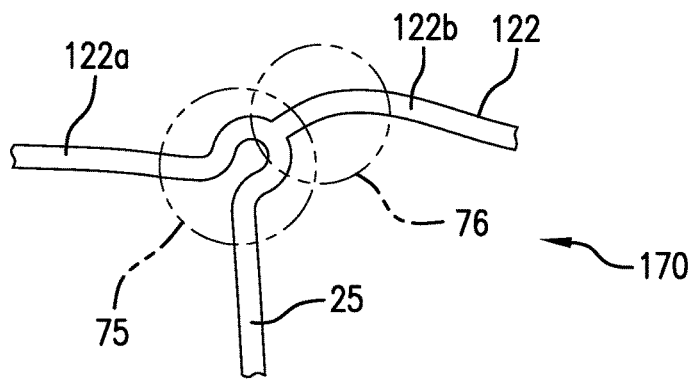

In another embodiment of a valve frame 120, depicted in FIGS. 3A and 3B, the novel pivot point 170 may be more complex, including a "horseshoe" connection 75 between the mast 25, 28a, 28b and a first segment 121a, 122a of a ring member 121, 122 and a diagonal connection 76 between the horseshoe member 75 and an adjacent segment 121b, 122b of the ring member 121, 122. FIG. 3A illustrates this valve frame 120 embodiment in its substantially flat unassembled configuration. FIG. 3B illustrates the pivot point 170 in greater detail. The orientation of the horseshoe 75 at the mast connection to the first ring member 121 is opposite to the orientation of the horseshoe connection 75 at the mast connection to the second ring member 122. Concomitantly, the orientation of the diagonal member 76 between the horseshoe member 75 and the adjacent segment of the first ring member 121 is opposite to the orientation of the diagonal connection 76 between the horseshoe member 75 and the adjacent segment of the second ring member 122. Compare 170a and 170b in FIG. 3A. Preferably, the orientation of the horseshoe member 75 and diagonal member 76 connecting masts to the first ring member 121 have the same orientation, and horseshoe member 75 and diagonal member 76 connecting masts to the second ring member 122 have the same orientation. The horseshoe member 75 at the pivot point 170 spreads displacements so that the strains are lower, and the diagonal connection 76 reduces angular displacements thus reducing strains. Optionally, the horseshoe-diagonal connection pivot point 170 may be the same width as the masts.

Alternatively, pivot points, whether S-shaped or horseshoe-diagonal or some other geometric shape, also, or instead, may have less thickness (e.g., smaller gauge)—in other words the portion that bends may be thinner than the mast or ring member structures in addition to or as an alternative to the favorable geometric pivot point shape. Connections between mast and ring members may alternatively include hinges.

Figure 4A:
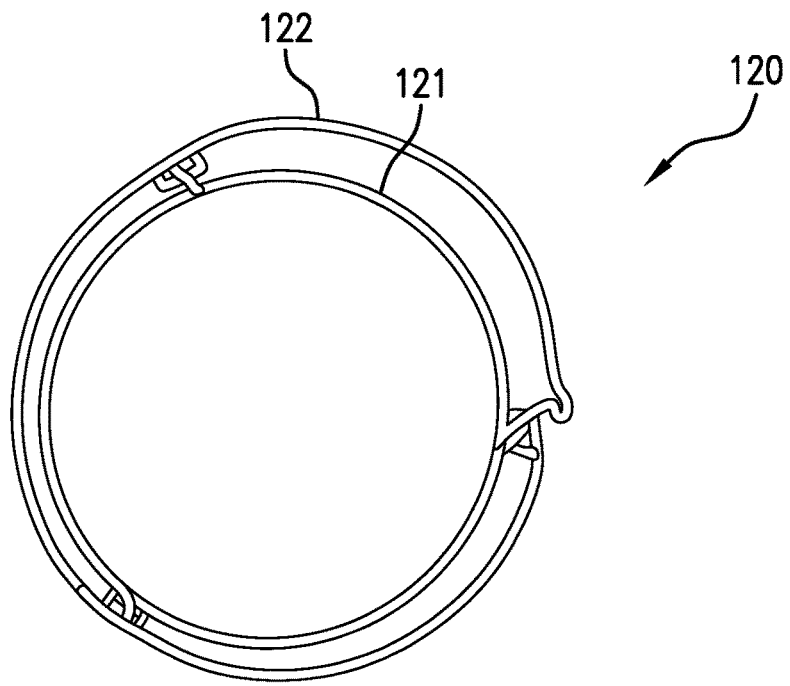
FIGS. 4A-B are photographs illustrating the embodiment of FIG. 3A valve frame in its working configuration.
Figure 4B:
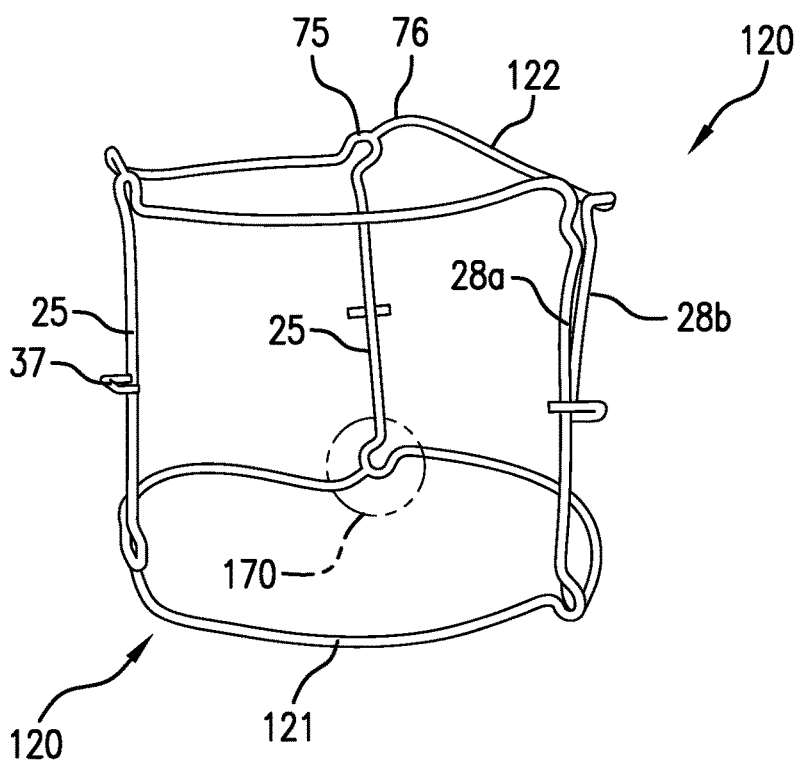

When the valve frame 120 of the embodiment of FIGS. 3A-B is in its working configuration, the horseshoe/diagonal pivot points 170 are planar. The planar construction of the embodiment of valve frame 120 is illustrated in FIG. 4A, which shows that viewed from the top, the valve frame appears as two round rings, which are the first ring member 121 and the second ring member 122. FIG. 4B depicts the embodiment of valve frame 120 with the horseshoe/diagonal pivot points 170 in its working configuration, viewed from the side. This perspective shows that the first and second ring members 121, 122 in this embodiment are not simple rings, but appear "wavy". Compare the first and second ring members of FIG. 4B to those in the embodiment illustrated in FIG. 2. Ring shafts 37 on the masts are also shown. Nevertheless, the ring members 121, 122 of the embodiment of FIGS. 3A-4B are substantially collinear to each other and the masts in the folded delivery configuration.

Figure 5:
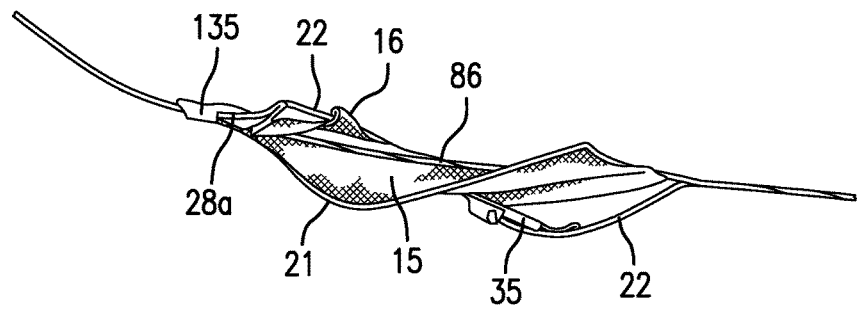
FIG. 5 is a photograph illustrating one way an embodiment of the double ring valve module may be folded according to the invention for loading into a delivery catheter.
Figure 6A:
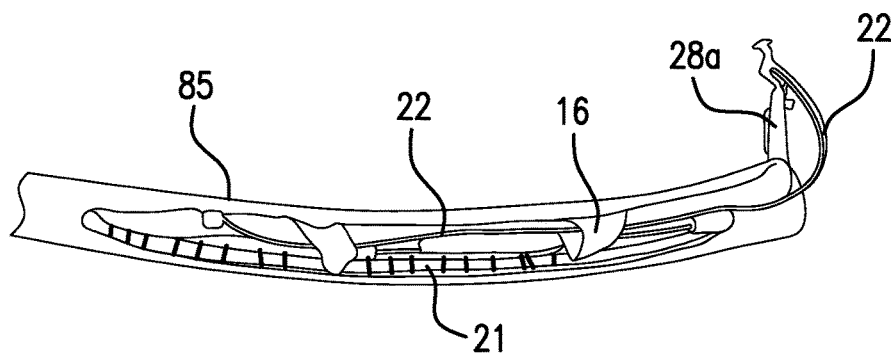
FIG. 6A is a schematic drawing of a photograph illustrating an embodiment of the double ring valve module folded according to the invention and loaded in a delivery catheter.
Figure 6B:
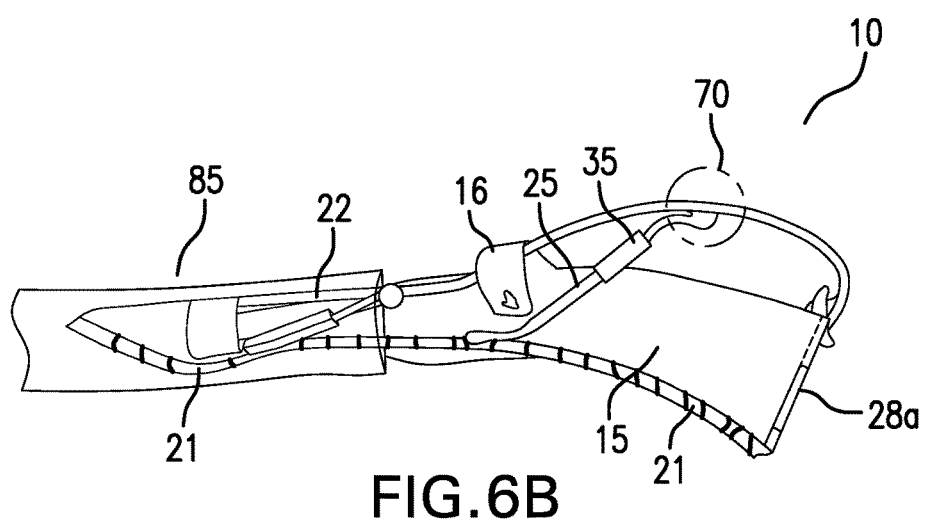
FIG. 6B is a schematic drawing of a photograph illustrating an embodiment of the double ring valve module during deployment from a catheter according to the invention.

To percutaneously deliver the valve module, the masts 25, 28a, 28b may be folded so that the substantially linear ring members 21, 22, 121, 122 and masts are oriented in the same general direction, to form a substantially collinear valve frame, and—with the valve leaflet(s) 15—may be wrapped in a spiral around a guide wire 86, as shown in FIG. 5. This method of folding the valve module permits the guide wire 86 to pass through the center of the spiraled linear valve frame and valve leaflets. A guide wire lumen may extend through the catheter 85 and the valve module 10 may be folded around the guide wire lumen or around the guide wire and, as shown in FIG. 6A, loaded in a catheter 85 (depicted as a clear tube for purposes of illustration) for delivery of the valve module. When the valve module 10 is deployed, the valve frame facilitates unfolding of the valve module (FIG. 6B) and the formation of a generally rounded shape (see FIGS. 7C, 7D). The capability of the masts to be folded down on the ring members to form the substantially collinear valve frame helps provide a minimized delivery diameter for the valve frame, and thus the valve module.

Figure 14A:
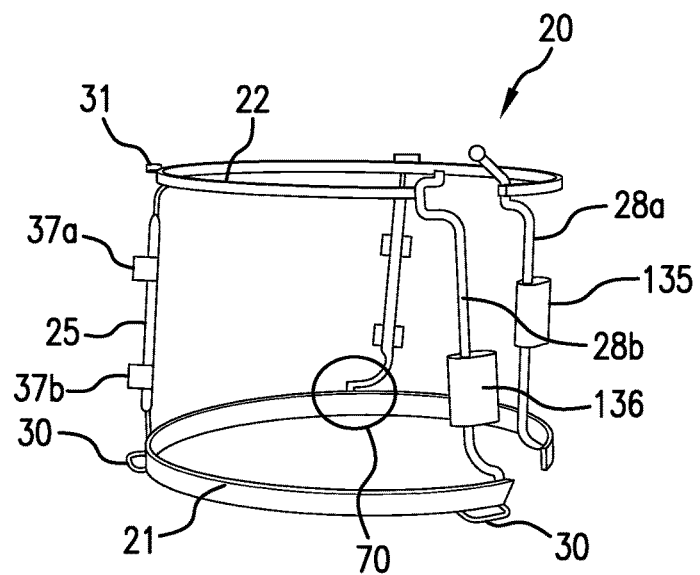
FIG. 14A is a schematic drawing of a photograph of an exemplary valve frame for a valve module in accordance with the invention.
Figure 14B:
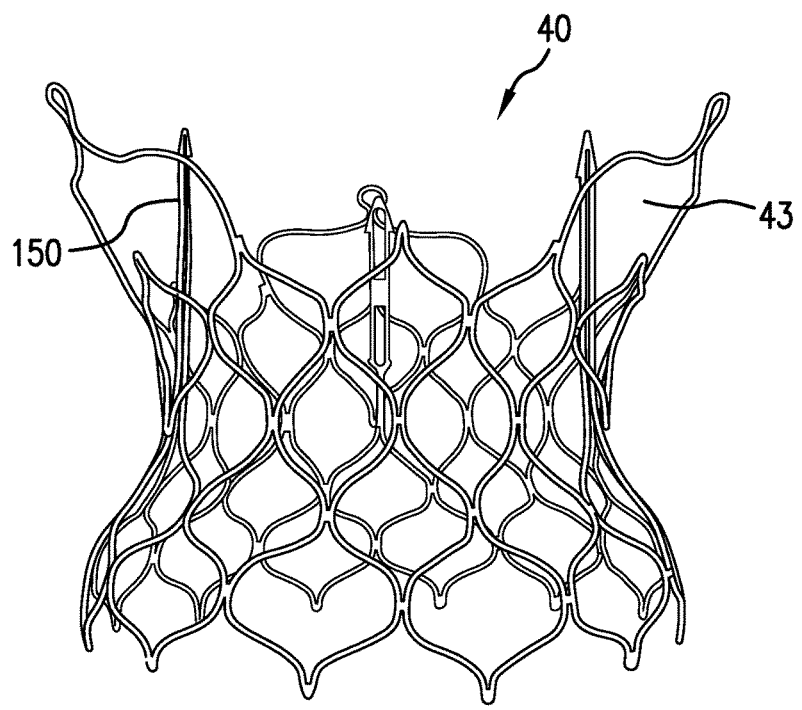
FIG. 14B is a schematic drawing of a photograph of an exemplary support module in accordance with the invention.
Figure 14C:
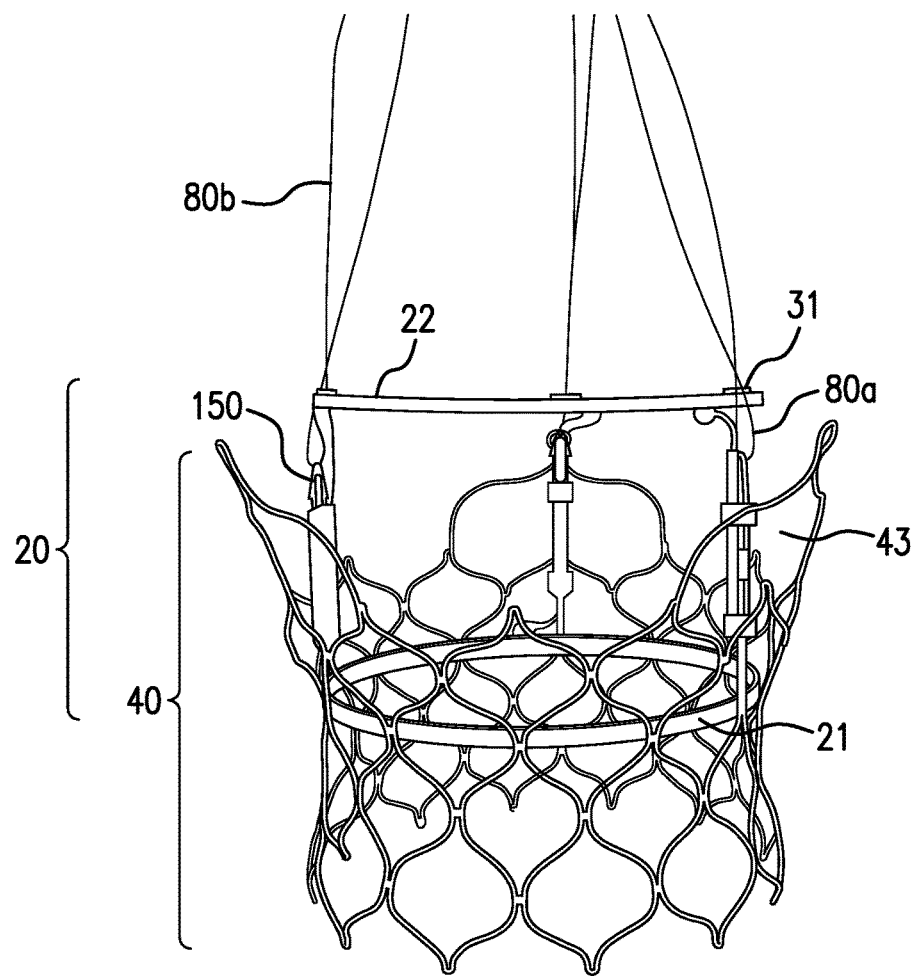
FIG. 14C is a schematic drawing of a photograph of another exemplary support module in accordance with the invention.
Figure 14D:
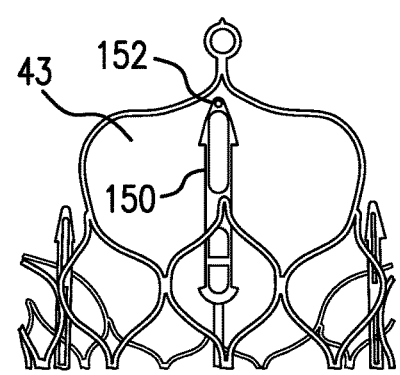
FIG. 14D is a schematic drawing of a photograph showing details of an embodiment of hybrid spear on an exemplary support module in accordance with the invention.

The support module may comprise a plurality of cells defined by filaments or struts, as shown in FIGS. 14B, 14D (see also FIGS. 7A-B, 8A, 10A). The plurality of cells may include one or more large cells 43, as shown in FIG. 14B (see also FIGS. 10A-B, 14C-D), to accommodate potential vascular intervention procedures that may be necessary in patients who have had the modular valve previously implanted. The larger cells 43 provide access through the implanted valve, for example, for catheters to be steered into coronary arteries.

When deployed, the support module should engage the valve annulus (or for example in an aortic valve replacement, the orifice of the left ventricle), pinning back the native valve leaflets, if not removed, so as to be secure therein so that the valve module does not shift in the lumen and is not displaced from the desired location, for example from the pressure of fluid flow through the valve or its impact on the closed valve. The support module may also enlarge the orifice of a stenotic valve. In one embodiment, the shape of the support module is annular with a uniform diameter, but it may be provided in other shapes too, depending on the cross-sectional shape of the lumen at the location the valve is to be implanted. Thus, for example, in its expanded configuration, the support module may have a non-uniform diameter along its longitudinal axis. The diameter of the proximal and distal ends of the support module may be the same or different. In one embodiment, illustrated in FIG. 14B, the support module may have a smaller diameter in the center region than at the proximal and distal ends. In such an embodiment, a longitudinal cross-section through the midline of the support module would have an hour glass or dog-bone shape. Such a shape may facilitate seating the support module in the valve annulus and/or improve sealing of the valve against the native anatomy.

As illustrated in FIGS. 7A-E, the system of the invention includes a delivery system 87, including a delivery device such as a catheter 85, for delivering the device modules in their low profile delivery configurations and from which the device modules may be deployed. The system also includes assembly wires 80 and pusher members 81, used for deploying and assembling the modular valve device of the invention.

The valve device of the invention may include a plurality of sets of locking members designed to lock the valve module to the expanded support module. Any of a variety of locking members may be used to lock the valve module to the support module, or for locking the ends of the unassembled valve module to one another. Examples of such locking members are described in detail in ¶¶83-111, 113 and FIGS. 7, 7A, 8A-14C of US 2010/0185275A1, incorporated herein by reference. Novel locking members, as described in more detail below, are preferred. Each set of locking members may comprise a first locking member and a second locking member. The first locking member of the locking member set may be attached to one of the masts of the valve frame and a second locking member of the locking member set may be attached to the support module. The first and second members of each set are circumferentially aligned with each other, and in a preferred embodiment, a wire guide is circumferentially aligned with a first locking member.

The first and second locking members may comprise a spear and a corresponding shaft having a lumen, wherein the spear has a first spear end and a second spear end, and a spearhead at the first spear end, the spearhead including an eyelet and an elongated aperture. Thus, in one embodiment employing novel locking members of the invention, the support module 40 has a plurality of spears 45, 145 at its distal end 42, which spears are designed to align with the plurality of shafts 35, 135, 136. In FIGS. 8A-B, 9A-B, 10A-B, shafts 35, 135, 136 or ring shafts 37 are located on the masts 25, 28a, 28b of the valve frame. In other embodiments, the shafts 35, 135, 136 or ring shafts 37 may be located on the one or more ring members 21, 22 of the valve frame, or the shafts 35, 135, 136 or ring shafts 37 may be located on a combination of masts and ring members. The spear and shaft embodiment of locking mechanism may be described generally with reference to the non-limiting embodiments of FIGS. 8A-B, 9A-B. Each spear 45 may have an eyelet 46 through which an assembly wire 80 may be threaded. See FIGS. 8B, 9B. Alternatively, the assembly wire 80 may be threaded through a portion of the support module (not shown).

In another embodiment, the spears 45 may be located on the valve frame, with the spearhead at the proximal end of the valve module, and the shafts 35, 135, 136 and/or ring shafts 37 may be located on the support module 40. In such embodiments, the valve module may be pushed into the support module along the assembly wires using push members, or pulled into the support module, as described in more detail below.

Figure 8A:
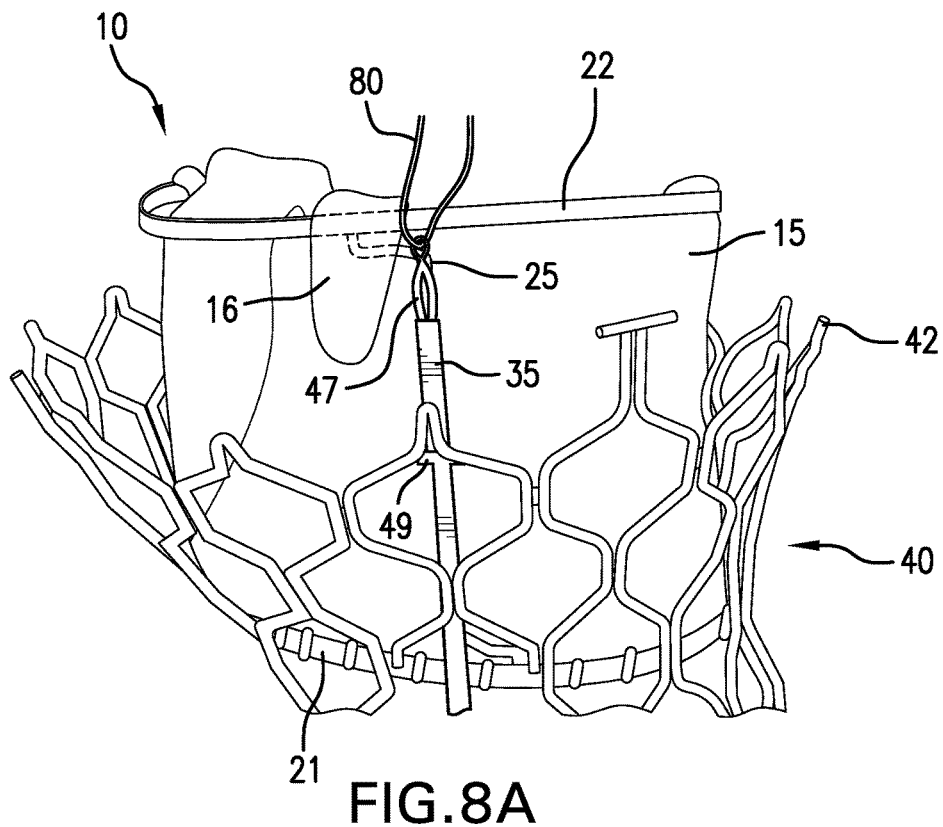
FIGS. 8A-B illustrate an embodiment of how the valve module and support module may be connected.
Figure 8B:
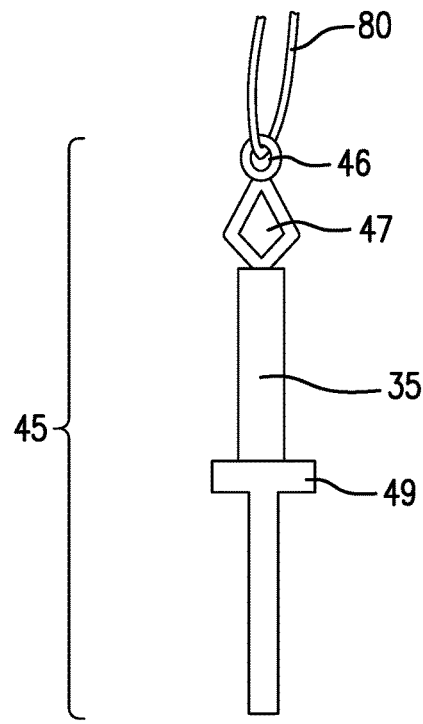

The spears 45 may include spearheads 47 having geometrical configurations that prevent the valve module from moving distally out of the support module, thereby locking the valve module to the support module. As illustrated in FIGS. 8A-B, the spearhead 47 comprises a flexible section, designed in this embodiment as a "kite". The spearhead 47 is shaped so as to flex to allow a shaft 35 to be eased over the spearhead 47 of the spear 45 using a pusher member 81 (see above, FIGS. 7D, 7E), but to prevent the shaft 35 from slipping back distally, thereby locking the valve module to the support module. Other geometric configurations also may be used, for example without limitation, diamond, circular, arrowhead, rivet, hook, ball/bulb and comparable shapes that permit unidirectional movement.

The assembly wire 80 is shown in FIGS. 8A and 8B looped through the eyelet 46 of the spear 45, and the shaft 35 is shown locked between the kite spearhead 47 at the distal end of the spear 45 and a spear cross 49 proximally. Alternatively, the assembly wire may be looped through an eyelet of one spear, around a portion of the support module and through the eyelet of an adjacent spear, or two adjacent spears, back up through a different wire guide, for example associated with a shaft corresponding to an adjacent spear. Such an arrangement decreases the number of required assembly wires for guiding the valve module to the support module. In a further alternative embodiment, the assembly wire may be looped through a portion of the support module, as described in one aspect in US 2011/0172784A1, incorporated herein by reference.

Where the valve frame includes a split mast, the split mast may include a pair of shafts, a first shaft 135 on the first half of the split mast (obscured), and a second shaft 136 on the second half of the split mast 28b, as illustrated in FIG. 9A. In this way, as the first and second shafts 135, 136 are eased over the spearhead 47, the first and second shafts 135, 136 simultaneously close the valve module to form the cylindrical working configuration. As in FIG. 8B, the spear 45 with spearhead 47 shown in FIG. 9B includes a spear cross 49 as a backstop, so that the valve module does not move proximally in the support module toward the heart. However in FIG. 9B, it is the wire guide 30, not the shafts, that abut the spear cross 49 and "seat" the shafts on the spear 45.

Figure 10A:
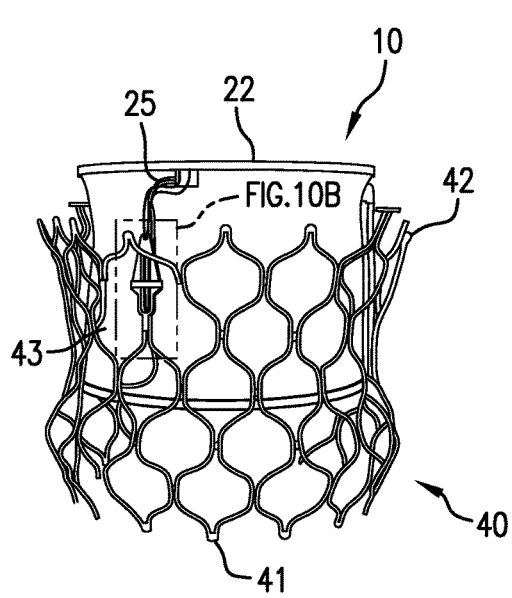
FIGS. 10A-B illustrate an embodiment of novel locking members.
Figure 10B:
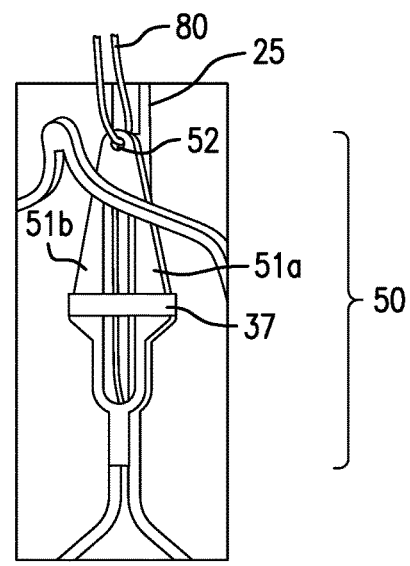
Figures 11A, 11B, 11C:
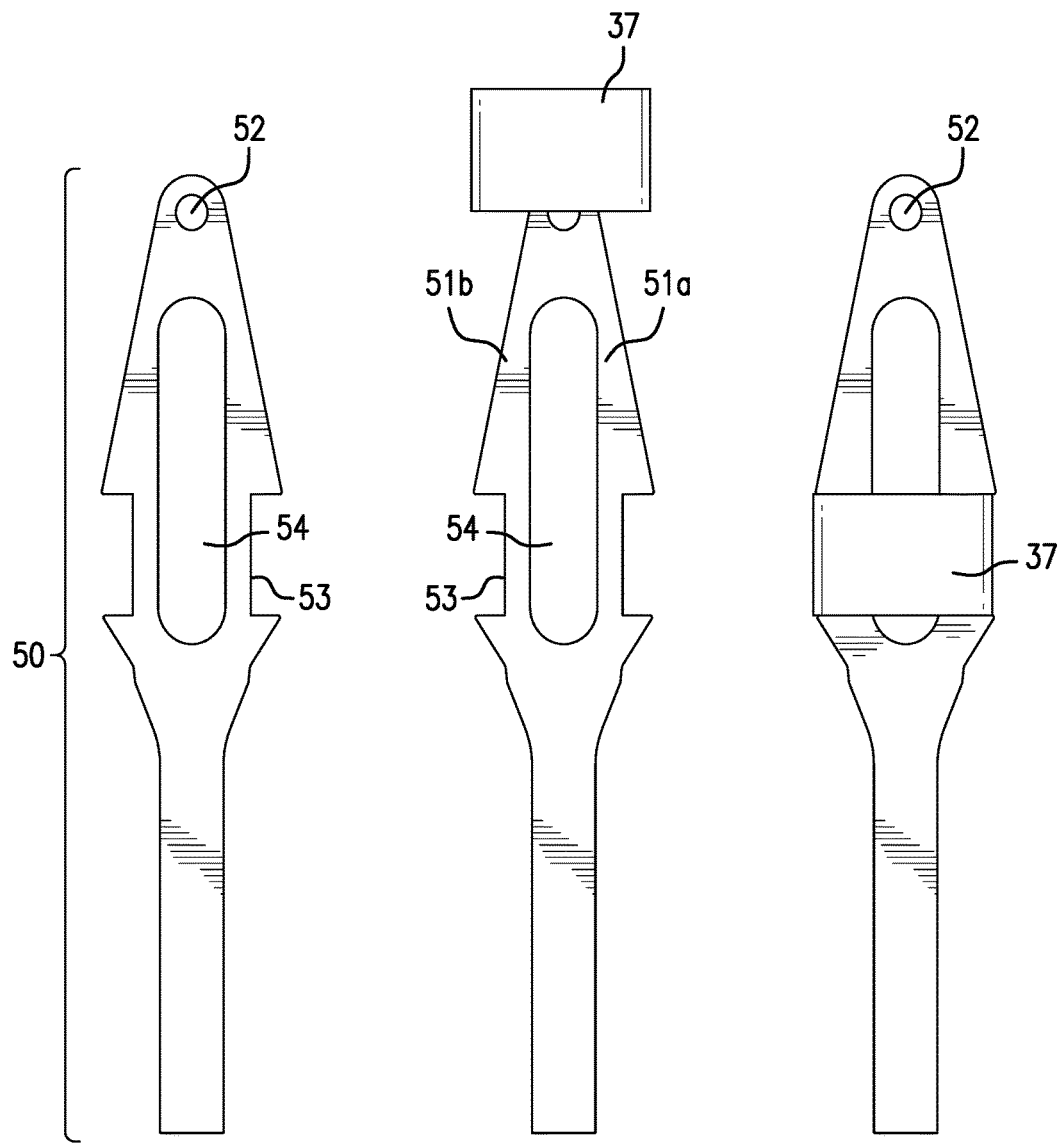
FIGS. 11A-C.

In another embodiment of the spear-shaft locking members, illustrated in FIGS. 10A-B, the spear is a hybrid spear 50, and a ring shaft 37 may be eased over a hybrid spear 50 to lock the valve module to the support module. The details of one embodiment of the hybrid spear 50 are shown in FIGS. 11A-C, the main structural elements being separated segments and a groove. The hybrid spear 50 includes segments 51a, 51b separated by an elongated aperture 54, which elongated aperture 54 permits the segments 51a, 51b to flex slightly toward one another as the ring shaft 57 is slid over it, and a groove 53 into which the ring shaft 37 may come to rest, thereby locking the ring shaft 37 on the hybrid spear 50. In the embodiment depicted in FIGS. 11A-C, there are two segments, however a hybrid spear having more than two segments is within the scope of the invention. FIG. 11A shows the eyelet 52, segments 51a, 51b, and groove 53. FIG. 11B shows a ring shaft 37 being eased onto the hybrid spear 50. FIG. 11C shows the ring shaft set in the groove 53 (obscured by the ring shaft) of the hybrid spear 50, thereby locking the valve module to the support module.

In yet another embodiment of locking members, illustrated in FIGS. 12A-B and 13A-B, a one-sided hybrid spear 60 comprising a spearhead 61 and stem region 68 that cooperates with a plurality of ring shafts 66, 67 and/or shafts 65a, 65b to lock the valve module to the support module. The spearhead 61 includes two segments separated by an elongated aperture 64 and a single groove 63 on the outer edge of one of the segments and an eyelet 62. The spear head 61 of the one-sided spear 60 may have a smaller diameter than the stem 68 and/or be tapered from a first end, where the eyelet 62 is located, toward the groove 63, but flares on one side to produce a wedge shape just above the groove 63 visible in FIGS. 12B, 13B. The diameter or width of the spear head 61 at the wedge does not exceed the diameter or width of the stem 68. An assembly wire may be threaded through the eyelet 62 at the top of the spear head 61.

Figure 12A:
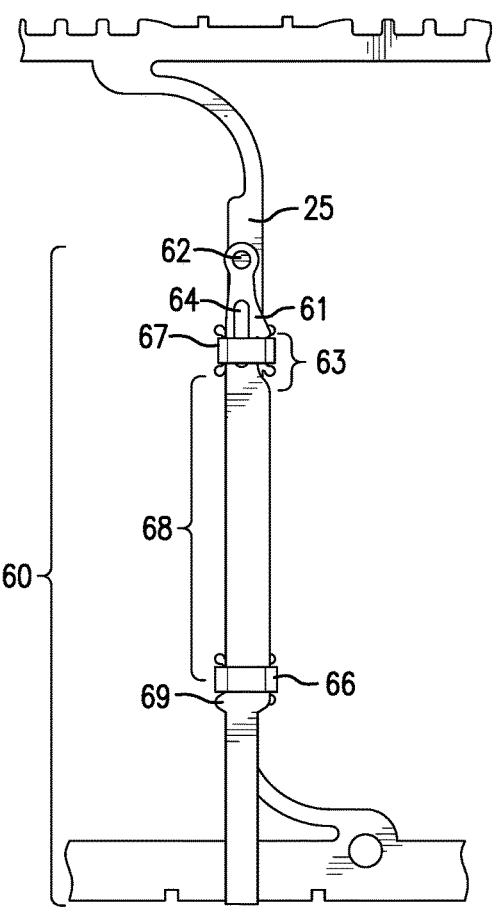
FIGS. 12A-B schematically illustrate an embodiment of a single groove hybrid spear.
Figure 12B:
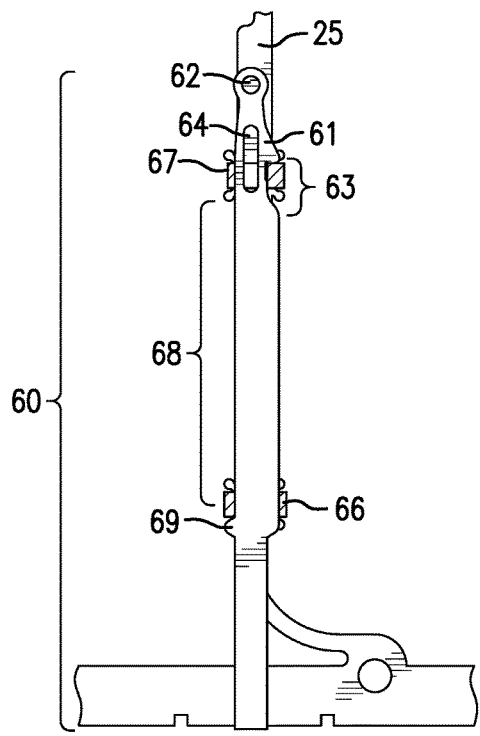

FIGS. 12A-B illustrate a one-sided spear 60 locked into ring shafts 66 and 67 (single-groove snap lock), which are attached to a mast 25. FIG. 12A shows a lower or first ring shaft 66 on the stem region 68 of spear 60 and an upper or second ring shaft 67 in a groove 63 of the spear head 61. The spear 60 includes at the base of the stem region 68, a spear stop 69, which limits the advance of the lower first ring shaft 66 over the spear 60. FIG. 12B is a cut-away view, revealing the structure of the spear head 61, which includes two segments join at each end that define an aperture 64. On the outer edge of one of the segments is a groove 63. FIG. 12B also illustrates the inner structure of the lower and upper ring shafts 66, 67. The ring shafts 66, 67 have lumens with diameters large enough for the spear 60 to fit on. The lumen diameter of the first ring shaft 66 is substantially the same as the width of the stem region 68. The lumen diameter of the second ring shaft 67 is smaller than the width of the stem region 68, and substantially the same as the width or diameter of the spearhead 61 at the point of the groove 63, allowing it to lock into the single groove 63 of the spear 60.

Figure 13B:
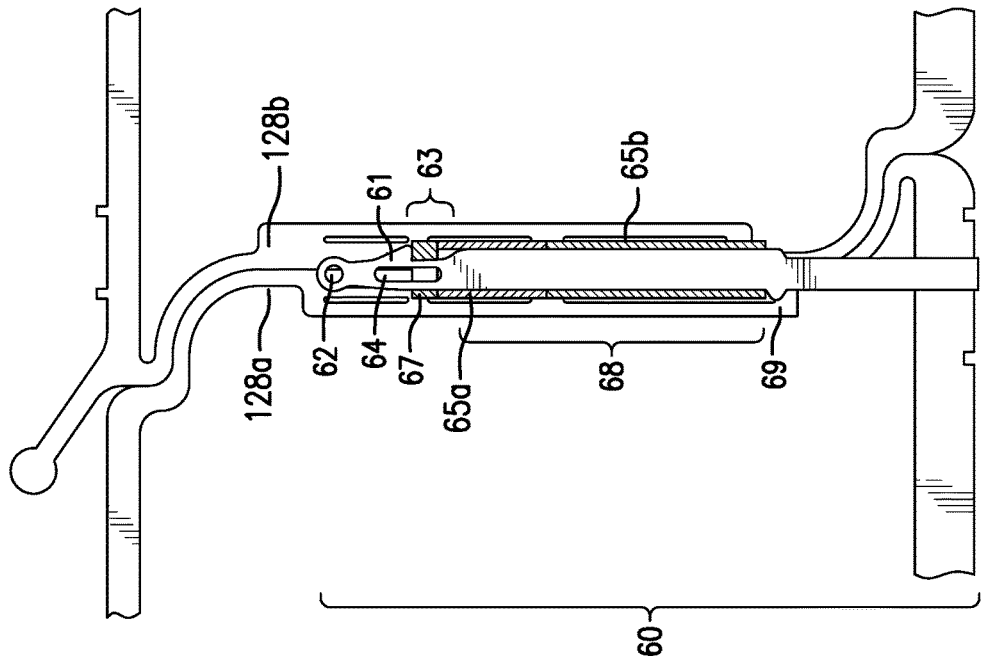
FIGS. 13A-B schematically illustrate an embodiment of a single groove hybrid spear.
Figure 13A:
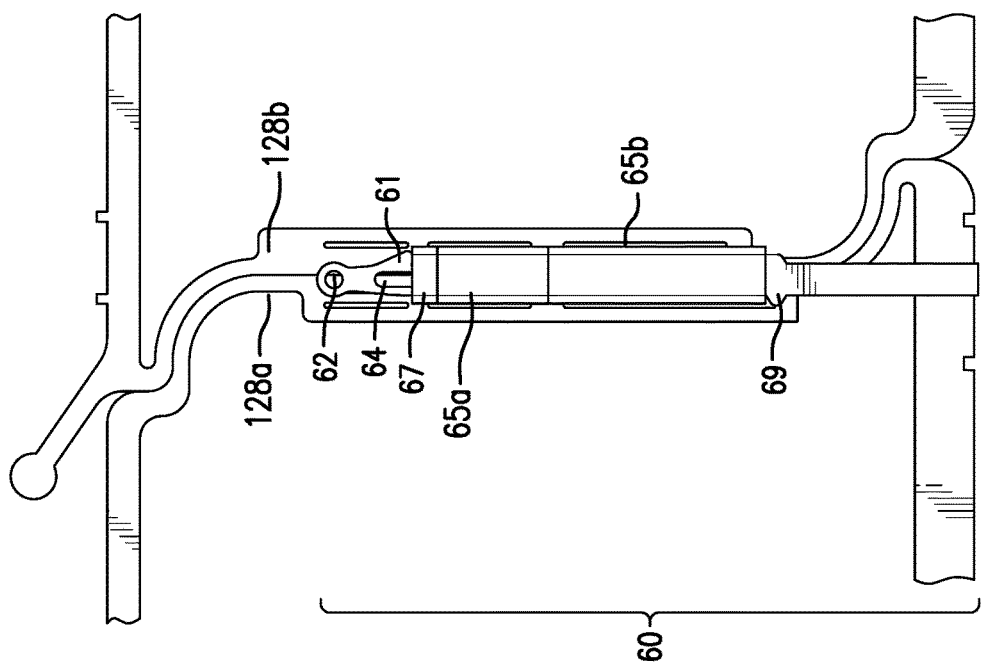

A one-sided spear 60 is particularly useful in conjunction with shafts on split masts 128a, 128b, as illustrated in FIGS. 13A-B. The spear 60 of FIGS. 13A-B is the same as spear 60 in FIGS. 12A-B, but the shafts differ to accommodate the split masts 128a, 128b. As depicted in FIG. 13A split mast 128a may have a shaft 65a and a ring shaft 67 attached to it, and split mast 128b may have a shaft 65b attached to it, all of which shafts 65a, 65b and ring shaft 67 may be slid over the spear 60 to lock the sides of the valve module together and lock the valve module to the support module. FIG. 13B is a cut-away view, revealing the structure of the spear head 61, as in FIG. 12B—the two segments that define an aperture 64 and groove 63 on the outer edge of one of the segments. FIG. 13B also illustrates the inner structure of the shafts 65a, 65b and ring shaft 67. The lumen diameters of the shafts 65a, 65b are substantially the same as the width or diameter of the stem region 68 of spear 60. The lumen diameter of ring shaft 67 is smaller than the width or diameter of the stem region 68, and substantially the same as the width or diameter of the spearhead 61 at the point of the groove 63, allowing it to lock into the single groove 63 of the spear 60. In one aspect of this embodiment ring shaft 67 and shaft 65b may be located on one half of the split mast 128b and shaft 65a may be located on the other half of the split mast 128a. In an alternative aspect, what is depicted in FIGS. 13A-B as ring shaft 67 may be a region of shaft 65a with smaller inner diameter, located on one half of the split mast 128a and shaft 65b may be located on the other half of the split mast 128b. Other combinations of shafts and ring shafts may be used with the split masts 128a, 128b, but all ring shafts/shafts have a diameter large enough to slide over the stem region 68 of spear 60, except for the one that fits into the single groove 63.

In either embodiment, where the single groove, one-sided spear 60 is used with a mast 25 or split masts 128a, 128b, the maximum width/diameter of the spear head 61 flare or wedge is not greater than the width/diameter of the stem region 68 and the elongated aperture 68 functions to allow at least one segment of the spear head 61 to flex toward the other upon application of stress. Thus, the shafts or ring shafts 65a, 65b, 66 with the larger lumen diameter may readily slide over the spear head 61 without flexing the segments of the spear head toward the elongated aperture 63. The ring shaft 67 (or ring shaft portion of a shaft), by contrast, having a narrower lumen diameter causes at least the segment of the spearhead 61 having the flare or wedge to flex, and subsequently the ring shaft 67 comes to rest in the groove 63. More particularly, the first ring shaft 66, the lower shaft having the larger luminal diameter, is eased over the spear 60 first, but pushing on a pusher 81. The segments on either side of the elongated aperture 64 does not flex as the first ring shaft 66 is slid over it, in view of the luminal diameter of the first ring shaft 66. The second ring shaft 67, the upper ring shaft having the smaller lumenal diameter, is then pushed over the spear head using the pusher 81. The elongated aperture 64 of the spearhead permits flexing of a segment on at least one side of the aperture 64 where the wedge is located, so that the second ring shaft 67 can be pushed over the largest flare of the taper, the wedge. The luminal diameter of the second ring shaft 67 designed to be closely matched to the width of the groove 63, and second ring shaft 67 the snaps into the single groove 63 of the one-sided hybrid spear 60.

An advantage of the one-sided spear 60 in combination with ring shaft 67 and shafts 65a, 65b, 66 over, for example a hybrid spear as illustrated in FIGS. 10A-B and 11A-C, is it permits a narrower outer diameter for both spear and shaft, which in turn reduces the overall profile of the valve module. Another advantage is that less force is required to push the spear through the shafts.

As locking members, the shafts and ring shafts are designed to interact with the spears to seat the valve module in the support module and lock the two device modules together, and/or to close the first and second ends of the valve module. Various combinations of spears, shafts and ring shafts may be used. Other locking members may be used in the alternative or in combination with the spears and shafts described herein, and the pushers similarly may be used to engage the locking members in addition to advancing the valve member over the assembly wires.

In certain embodiments, the wire guides may have an additional function. Where the pushers are used to advance the valve module into the support module and to engage locking members, the wire guide 31 on the second ring may provide a surface upon which the pushers exert force. Using the wire guides for this purpose may provide the following, non-limiting, advantages of avoiding damaging the leaflet tissue and/or preventing the pushers from slipping off a ring surface. Similarly, where shafts are located on valve modules, the distal end of the shafts may be used as a surface against which the pusher members push the valve member. In some embodiments, a wire guide also may serve as a "seat" against the spear cross once the shafts are fully engaged on the spear (see e.g., FIG. 9B).

Referring back to FIGS. 7A-E, which depict the system of the invention, a method of deploying and assembling the modular valve device of the invention is illustrated. In this embodiment, an assembly wire 80 is threaded through the wire guide 31 and looped through the eyelet of the spear and doubled back, so that the assembly wire 80 is a double wire through the wire guides prior to loading the device modules into the delivery system. See FIGS. 8A-B, 9A-B, and 10B. In this way, after the support module 40 has been deployed, expanded and anchored at the location of valve implantation, the valve module 10 may be deployed from the delivery device, unfolded and made to ride down the assembly wires 80 toward and into the support module 40. See FIGS. 7A-E. In another embodiment, the assembly wire may be threaded through the eyelet of one spear, around the support module through an eyelet of another spear and back up through another wire guide. Such an arrangement decreases the number of assembly wires required and preserves the ability to pull on one end of the assembly wire for removal.

Pusher members 81 may be slid over the assembly wires 80 and used to push the valve module 10 along the assembly wires 80. Pusher members 81 may be, for example, hollow tubes through which the assembly wires 80 are threaded, and which may be manipulated via the delivery system 87. Pusher members 81 may be used to deploy the valve module from the catheter and/or to assist in assembling the valve module 10 and lock it to the support module 40. In any of these uses, the assembly wires 80 are held at tension, so that the valve module 10 may glide over the assembly wires as though on rails. Wire guides 31 may be used not only to orient the valve module 10 relative to the support module 40, but also in conjunction with the pusher members 81 to connect/attach the valve module 10 and support module 40.

In another embodiment (not shown), each spear and its eyelet may be located on the valve module, with the spearhead at the proximal end of the spear, and the shaft may be located on the support module. In this embodiment, the catheter may be advanced through the support module past the proximal end 41 (see FIG. 10A) of the support module and used to pull on the assembly wires thereby pulling the valve module into the support module and the spears into the shafts. In still another embodiment, the spears may be located on the valve module and the shafts on the support module, and the method may include advancing the catheter beyond the proximal end 41 of the support module 40 and using the assembly wires 80 (and optionally pusher members 65) to pull the valve module 10 toward and into the support module 40.

Once the valve module and support module are assembled and locked together, because each assembly wire 80 is a double wire, one end of the assembly wire 80 may be pulled to disengage the assembly wire from the implanted, assembled valve device.

A method of deploying and assembling the modular device using the system of the invention may proceed as follows: advancing the delivery device so that its distal end is near a selected location, for example the location of valve implantation; deploying the support module from the delivery device; expanding the support module at the selected location (where the support module is not self-expanding); deploying the valve module from the delivery device; advancing the valve module along the assembly wires toward the support module using the pusher members; and moving each of the plurality of shafts over the corresponding spear to lock the valve module to the support module. The moving step may also include moving the first and second shafts of the split mast over the spear (or moving the spears into the shafts if the location of the spears and shafts on the device modules is reversed) to form a working configuration valve module. In another embodiment, the valve module may be deployed before the support module, and advanced into the support module after the support module is seated in the native valve annulus. In this alternative method, the catheter containing the support module may be advanced through the deployed valve module and deployed, either the catheter advanced further, and then the valve module may be pulled onto the support module, or the catheter may be withdrawn and pushers used to glide the valve module over the assembly wires onto the support module.

As illustrated in FIG. 7A, the support module 40 has been deployed and expanded at a selected location in a vessel 90 (the blood vessel depicted as a clear tube for purposes of illustration) and the catheter 85 withdrawn to provide space for deploying the valve module 10. The assembly wires 80 are held taut, for example at a tension. FIG. 7B illustrates the folded valve module being deployed from the catheter 85, the first ring member 21 visible with the valve leaflet attached. In FIG. 7C, the valve module has been deployed and is unfolded, but not yet in a working configuration. The first ring member 21, second ring member 22, a mast 25, first and second halves of a split mast 28a, 28b, and the valve leaflet 15 are visible. The assembly wires 80 are shown taut between the support module 40, threaded through the wire guides (not shown) of the valve module and into the catheter 85. FIG. 7D illustrates the pusher members 81 being deployed from the delivery system 87, the assembly wires 80 still held at tension. FIGS. 7D and 7E show how the pusher members 81 may be used to push the valve module 10 into the support module 40.

In certain embodiments, the deployed and unfolded valve module may be pulled into the support module via the assembly wires by a method that further includes advancing the delivery device, for example a catheter, distally through the deployed valve module and the deployed and expanded support module to a point distal of the support module (i.e., beyond the proximal end of the support module) and pulling the assembly wires. The shafts may be pulled over the spear heads of the spears to engage the shafts and spears by further pulling the assembly wires. Alternatively, the pushers may be used to pull the valve module into the support module and the shafts over the spearheads. In this aspect of the method, the pushers are extended beyond the distal end of the catheter, i.e., well beyond the proximal end of the support module. Advancing the pushers in this manner effectively pulls on the taut assembly wires, thereby pulling the valve module into the support module and effecting locking of the locking members, such as pulling the shafts over the spearheads. In such embodiments, the spears may be located on the valve frame, with the spearhead at the proximal end of the valve module, and the shafts and/or ring shafts located on the support module.

FIGS. 14A-D are provided to illustrate the structures of the valve module and support module of the invention. FIG. 14A is a schematic drawing based on a photograph illustrating an embodiment of a valve frame 20 for a valve module in accordance with the invention. The details of valve frame 20 are depicted without the valve leaflets attached. In this embodiment the valve frame 20 has a first ring member 21, a second ring member 22, a plurality of masts 25, including a split mast, comprising split mast halves 28a, 28b, and pivot points 70. In this embodiment, the first ring member 21 is wider (longitudinally) than the second ring member 22, but has the same radial thickness. Also shown is one of a plurality of first wire guides 30 on the first ring member 21 and one of a plurality of second wire guides 31 on the second ring member 22, the second wire guides 31 having a surface (as depicted, a flat surface) for pushing members to push against. Exemplary locking members are also depicted. Specifically, first and second ring shafts 37a, 37b are located on each mast 25, first shaft member 135 on the first split mast half 28a and a second shaft member 136 located on the second split mast 28b half.

FIGS. 14B and 14C are schematic drawings based on photographs depicting embodiments of a support module 40 in accordance with the invention. These particular embodiments include spears 45 and one or more large cells 43, as discussed above. The large cells 43 are preferably positioned at the distal end of the support module in embodiments intended to be implanted to replace an aortic valve, where they may sit adjacent coronary arteries and provide access thereto. In other embodiments, the position of large cells 43 and their size can be adjusted to accommodate the position and size of vessels to which catheter access may be desirable after implantation of the valve device. The support module 40 embodiment depicted in FIG. 14B has a middle section with a narrower diameter than the proximal and distal sections, e.g., "hour-glass" shaped, as discussed above. The support module 40 embodiment depicted in FIG. 14C has a wider diameter at its distal end than at its proximal end, e.g., "pear" shaped. FIG. 14C further illustrates a valve frame 20, having a first and second ring member 21, 22, locked to the support module 40 using an embodiment of hybrid spears 150 and shafts and ring shafts. The connections are more readily viewed without valve leaflets attached to the valve frame. Assembly wires 80a, 80b are also shown, in particular assembly wire 80a is shown looped through an eyelet of a hybrid spear and a wire guide 31 on the second ring 22. FIG. 14D is a schematic drawing based on a photograph illustrating details of an embodiment of a hybrid spear 150 on a support module, including the eyelet 152. A large cell 43 of the support module is also shown. The embodiment of a hybrid spear 150 in FIGS. 14B-D is different from the hybrid spear 50 depicted in FIGS. 11A-C, but functions similarly with ring spears.

It will be appreciated by persons having ordinary skill in the art that many variations, additions, modifications, and other applications may be made to what has been particularly shown and described herein by way of embodiments, without departing from the spirit or scope of the invention. Therefore it is intended that scope of the invention, as defined by the claims below, includes all foreseeable variations, additions, modifications or applications.

What is claimed is:

1. A valve module for a percutaneous modular valve device, comprising:
    a valve frame; and
    a plurality of valve leaflets attached to said valve frame;
    wherein said valve frame comprises a first ring member and a plurality of masts connected to and extending from said first ring member, wherein connections between said plurality of masts and said first ring member are pivot points;
    wherein said valve frame has a folded unassembled delivery configuration and is designed to be assembled into a working configuration after deployment from a delivery device.

2. The valve module of claim 1, wherein one of said plurality of masts is a longitudinally split mast having a first mast half and a second mast half.

3. The valve module of claim 2, wherein said valve leaflets are attached to the longitudinally split mast and are not attached to the other masts.

4. The valve module of claim 1, wherein said valve leaflets are scrunched in said folded unassembled delivery configuration.

5. The valve module of claim 1, wherein said pivot points are contained in said plurality of masts.

6. The valve module of claim 1, wherein the valve frame further comprises a second ring member, said plurality of masts connected to said second ring member, said plurality of masts disposed between said first ring member and said second ring member, wherein connections between said plurality of masts and said second ring member are pivot points.

7. The valve module of claim 6, wherein said valve leaflets are attached to said first ring member and suspended from said second ring member.

8. The valve module of claim 7, wherein said valve leaflets are sewn to said first ring member.

9. The valve module of claim 7, further comprising a leaflet loop coupling said valve leaflets to said second ring member.

10. The valve module of claim 9, wherein said leaflet loop is formed of the same material as said valve leaflets.

11. The valve module of claim 6, wherein said first and second ring members are substantially linear in said folded unassembled delivery configuration.

12. The valve module of claim 6, wherein said first ring member is wider than said second ring member along a longitudinal axis of said working configuration valve module.

13. The modular valve of claim 6, wherein one or both of said first and second ring members comprises a wire guide.

14. The valve module of claim 1, wherein said valve frame is biased to said working configuration.

15. The valve module of claim 14, wherein said valve frame is formed of a shape-memory material.

16. The valve module of claim 1, wherein said valve leaflets comprise a first material and are attached to said valve frame via a sandwich attachment with a second material.

17. The valve module of claim 1, wherein said pivot points are selected from the group consisting of S-shaped and horseshoe shaped.

18. The valve module of claim 1, wherein said plurality of masts are spirally wound around a guide wire in said folded unassembled delivery configuration.

19. A modular percutaneous valve device comprising the valve module of any one of claims 1-18, further comprising:
    a support module, said support module having a compressed delivery configuration and an expanded working configuration; and
    a plurality of complementary locking members for locking said valve module and said expanded support module to one another.

20. The modular valve device of claim 19, wherein each of said complementary locking members comprises a spear and a shaft, said spear having a first end and a second end, said shaft fitting over said spear.

21. The modular valve device of claim 20, wherein at least one of said spears includes a spearhead at said first end and a spear cross at said second end.

22. The modular valve device of claim 21, wherein said spearhead has a shape selected from the group consisting of: a diamond-shape, a rhombus, a trapezoid, a kite, a circle, a rectangle, an oval, an arrowhead, a sphere, an ovoid, and a bulb.

23. The modular valve device of claim 20, wherein at least one complementary shaft and spear comprises a ring shaft and a hybrid spear.

24. The modular valve device of claim 23, wherein the spear further comprises an eyelet on a free end thereof, the eyelet configured to receive an assembly wire therethrough.

25. A percutaneous modular valve device, comprising:
   a valve frame comprising a first ring member and a plurality of masts;
   a support module having a compressed delivery configuration and an expanded working configuration; and
   a plurality of complementary locking members, wherein each of said complementary locking members comprises a spear located on said support module and a shaft located on a complementary mast of the plurality of masts of said valve frame, said shaft fitting over said spear to lock said valve frame and said support module to one another.

26. The modular valve device of claim 25, wherein at least one of said spears includes a spearhead at a first end and a spear cross at a second end.

27. The modular valve device of claim 25, wherein at least one complementary shaft and spear comprises a ring shaft and a hybrid spear.

28. The modular valve device of claim 25, wherein at least one complementary shaft and spear comprises a first ring shaft having a first internal diameter, a second ring shaft having a second internal diameter, and a one-sided hybrid spear.

29. The modular valve device of claim 25, wherein said valve frame further comprises a second ring member, said plurality of masts connected to and disposed between said first and second ring members.

30. The modular valve device of claim 29, wherein one of said plurality of masts is a longitudinally split mast having a first mast half and a second mast half, wherein said first mast half includes a first shaft and said second mast half includes a second shaft, said first shaft located proximal of said second shaft along a longitudinal axis of said valve frame.

31. The modular valve device of claim 25, wherein said spear is a hybrid spear comprising an elongated aperture extending therethrough and a first groove extending along a first side thereof, and wherein the shaft is a ring shaft.

32. The modular valve device of claim 31, wherein said hybrid spear comprises a second groove located on a second side thereof.

33. The modular valve device of claim 31, wherein said hybrid spear comprises a spear stop sized to prevent movement of the shaft therepast.

* * * * *